United States Patent
Kopelman et al.

(10) Patent No.: US 6,636,652 B1
(45) Date of Patent: Oct. 21, 2003

(54) OPTICAL SENSORS FOR THE DETECTION OF NITRIC OXIDE

(75) Inventors: Raoul Kopelman, Ann Arbor, MI (US); Heather Clark, Middletown, CT (US); Susan Barker, Silver Spring, MD (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/365,487

(22) Filed: Aug. 2, 1999

(51) Int. Cl.$^7$ ................................................. G02B 6/00
(52) U.S. Cl. ........................ 385/12; 385/38; 385/127; 385/128
(58) Field of Search ............................ 385/12, 33, 38, 385/43, 123, 127, 128, 141–145; 359/368, 385; 250/227.14, 227.11; 427/162, 163, 457, 487; 435/68, 4, 176, 6, 91.2; 536/22.1, 23.1, 24.3, 24.5

(56) References Cited

U.S. PATENT DOCUMENTS

| | | | | |
|---|---|---|---|---|
| 4,621,052 A | * | 11/1986 | Sugimoto ..................... | 435/68 |
| 5,361,314 A | * | 11/1994 | Kopelman et al. ............ | 385/12 |
| 5,606,638 A | * | 2/1997 | Tymianski et al. ........... | 385/143 |
| 5,627,922 A | * | 5/1997 | Kopelman et al. ............ | 385/12 |
| 6,002,817 A | * | 12/1999 | Kopelman et al. ............ | 385/12 |
| 6,272,262 B1 | * | 8/2001 | Kopelman et al. ............ | 385/12 |
| 6,287,765 B1 | * | 9/2001 | Cubicciotti .................... | 435/6 |

OTHER PUBLICATIONS

Blyth et al., "Sol–Gel Encapsulation of Metalloproteins for the Development of Optical Biosensors for Nitrogen Monoxide and Carbon Monoxide," *Analyst*, 120:2725–2730 (1995).

Diodati et al., "Complexes of Nitric Oxide with Nucleophiles as Agents for the Controlled Biological Release of Nitric Oxide: Antiplatelet Effect," *Thrombosis and Haemostasis*, 70:654–658 (1993).

Marletta et al., "Unraveling the biological significance of nitric oxide," *Biofactors*, 2:219–225 (1990).

Oliveira et al., "A Heme–binding Protein from Hemolymph and Oocytes of the Blood–sucking Insect,*Rhodiusprolixus*", *J. Biol. Chem.* 270:10897–10901 (1995).

Ribeiro et al., "Reversible Binding of Nitric Oxide by a Salivary Heme protein from a Bloodsucking Insect," *Science*, 260:539–541 (1993).

Snyder, "Janus faces of nitric oxide," *Nature*, 364:577 (1993).

Stone and Marletta, "Soluble Guanylate Cyclase from Bovine Lung: Activation with Nitric Oxide and Carbon Monoxide and Spectral Characterization of the Ferrous and Ferric States," *Biochemistry*, 33:5636–5640 (1994).

Tsutsui and Mueller, "A protein with multiple Heme–binding sites from rabbit Serum," *J. Biol. Chem.*, 257: 3925–3931 (1982).

Valenzuela et al., "A Salivary Nitrophorin (Nitric–Oxide–Carrying Hemoprotein) In The Bedbug Cimex lectularius," *J. Exper. Biol.*, 198:1519–1526 (1995).

(List continued on next page.)

Primary Examiner—Frank G. Font
Assistant Examiner—Michael P Mooney
(74) Attorney, Agent, or Firm—Medlen & Carroll, LLP

(57) ABSTRACT

Optical fiber sensors and fiberless optical sensors for measuring analytes, and in particular nitric oxide, are described utilizing metals, and more particularly, metal colloids. Proteins (or fragments thereof) with selective binding are immobilized on metal particles. The proteins may be dye-labeled for increased sensitivity. Additionally, metals functionally linked to reporter dyes are described in addition to the incorporation of reference compounds for ratiometric measurements.

23 Claims, 20 Drawing Sheets

OTHER PUBLICATIONS

Zhou and Arnold, "Response Characteristics and Mathematical Modeling for a Nitric Oxide Fiber–Optic Chemical Sensor," *Anal. Chem.*, 68:1748–1754 (1996).

Garbor and Allon, "Spectro Fluorometric Method for NO Determination", *Anal. Biochem.*, 220:16–19 (1994).

Godwin and Berg, "A Fluorescent Zinc Probe Based on Metal–Induced Peptide Folding", *J. Am. Chem. Soc.* 118:6514–6515 (1996).

Handley, et al. "Colloidal gold–low density lipoprotien conjugates as membrane receptor probes", *Proc Nat Acad Sci, USA* 78:368–371 (1981).

De Roe, et al. "A model of protein—colloidal gold interactions", *J. Histochem. Cytochem.* 35:1191–1198 (1987).

Handley, et al. "Hepatic binding and internalization of low density lipoprotein–gold conjugates in rats treated with 17α–ethinylestradiol", *J. Cell Biol.* 90:778–787 (1981).

Geoghegan and Ackerman, "Adsorption of horseradish peroxidase, ovomuccoid and anti–immunoglobulin to colloidal gold for the indirect detection of concanavalin A, wheat germ agglutinin and goat anti–human immunoglobulin G on cell surfaces at the electron microscopic level: A new method, theory and application", *J. Histochem. Cytochem.* 25:1187–1200 (1977).

Broderick, et al. "Evidence for retention of biological activity of a non–heme iron enzyme adsorbed on a silver colloid: A surface–enhanced resonance Raman scattering study", *Biochemistry* 32:13771–13776 (1993).

Grabar, et al. "Kinetic control of interparticle spacing in Au colloid–based surfaces: Rational nanometer–scale architecture", *J. Am. Chem. Soc.* 118:1148–1153 (1996).

Freeman, et al. "Self–assembled metal colloid monolayers: An approach to SERS substrates", *Science* 267:1629–1632 (1995).

Graber, et al. "Preparation and characterization of Au colloid monolayers" *Anal. Chem.* 67:735–743 (1995).

Malinski and Czuchajowski, "Nitric Oxide Measurement by Electrochemical Methods" in *Methods in Nitric Oxide Research*, Freelisch and Stamler, eds., John Wiley and Sons, pp. 319–339 (1996).

Moncada, et al., "Nitric Oxide: Physiology, pathology and pharmacology" *Pharm Reviews* 43:109–142 (1991).

Ding, et al., "Release of reactive nitrogen intermediates and reactive oxygen intermediates from mouse peritoneal macrophages" *J. Immunol.* 141:2407–2412 (1988).

Xia and Zweier, "Substrate control of free radical generation from xanthine oxidase in the postischemic heart" *J. Biol. Chem.* 270: 18797–18803 (1995).

Zweier, et al., "Measurement and characterization of free radical generation in reoxygenated human endothelial cells" *Am. J. Physiol.* 266:C700–C708 (1994).

Bartsch, et al., "Preparation and properties of *Rhodospirillum rubum* cytochromes $c_2$, cc' and $b_{557.5}$ and flavin mononucleotide protein" *J. Biol. Chem* 246:4489–4406 (1971).

Ren and Meyer, "Atomic structure of a cytochrome c' with an unusual ligand–controlled dimer dissociation at 1 •8Å resolution" *J. Mol. Biol.* 234:433–445 (1993).

Taniguchi and Kamen, "On the anomalous interactions of ligands with Rhodospirillium heam protein (RHP)" *Biochimica et Biophysica Acta* 74:438–455 (1963).

Caffery, et al. "NMR assignment of *Rhodobacter capsulatus* ferricytochrome c', a 28kDa paramagnetic heme protein" *Biochemistry* 34:5904–5912 (1995).

Yoshimura, et al. "Identification of heme axial ligands of cytochrome c' from *Alcaligenes sp.* N.C.I.B. 11015" *Biochimica et Biophysica Acta* 831:267–274 (1985).

Yoshimura, et al. "Spectral properties of nitric complexes of cytochrome c' from *Alcaligenes sp.* NCIB 11015" *Biochemistry* 25:2436–2442 (1986).

Malinski and Taha, "Nitric oxide release from a single cell measured in situ by a porphyrinic–based microsensor" *Nature* 358:676–678 (1992).

Vallance, et al., "Direct measurement of nitric oxide in human beings" *Lancet* 364:153–154 (1995).

Kiechile and Malinski, "Indirect detection of nitric oxide effects: A review" *Ann. Clin. Lab. Sci* 26:501–511 (1996).

Pariente, et al. "Chemically modified electrode for the selective and sensitive determination of nitric oxide (NO) in vitro and in biological systems" *J. Electroanalyticl Chem.* 379:191–197 (1994).

Shibuki, "An electrochemical microprobe for detecting nitric oxide release in brain tissue" *Neurosci. Res.* 9:69–76 (1990).

Zhang, et al. "Electrochemical reduction of nitrite and nitric oxide catalyzed by an iron–alizarin complexone adsorbed on a graphite electrode" *Inorg. Chem.* 33:1392–1398 (1994).

Dave, et al. "Sol–gel encapsulation methods for biosensors" *Anal. Chem.* 66:1120A–1127A (1994).

Broderick and Taha, "Nitric oxide detection using a popular electrochemical sensor: Recent applications and the development of a new generation of highly sensitive and selective NO–microsensors." pp. 2–18, Presented at the satellite symposium, 4th IBRO World Congress of Neuroscience, Kyoto, Japan, 1995, World Precision Instruments.

Ichimori, et al. "Practical nitric oxide measurement employing a nitric oxide–selective electrode" *Rev. Sci. Instrum.* 65:2714–2718 (1994).

* cited by examiner

OPTICAL SENSORS FOR THE DETECTION OF NITRIC OXIDE

Fiber-Optic Chemical Sensor" *Anal. Chem.* 68:1748 (1996). This sensor was constructed by holding a small amount of an internal reagent solution at the tip of a fiber-optic bundle with a piece of gas-permeable membrane. Nitric oxide diffuses across the membrane into this internal solution, where a chemiluminescent reaction between nitric oxide, hydrogen peroxide, and luminol takes place. The drawbacks of this sensor include the following: 1) the response time (approximately 8–17 seconds) is longer than the time needed for nitric oxide in the solution to be converted to nitrite; 2) the detection of nitric oxide is complicated by interferences from dopamine, uric acid, ascorbic acid, and cysteine, 3) the sensor is relatively large in size (greater than 6 mm in diameter) and thus difficult to use for the measurement of cellular nitric oxide levels (and impossible for intracellular measurements); and 4) the sensor has relatively poor sensitivity, i.e., a relatively high limit of detection (approximately 1.3 mM of nitric oxide).

Sensors involving sol-gel technology have also been attempted. The process involves hydrolyzing an alkoxide of silicon to produce a sol, which then undergoes polycondensation to form a gel. Biomolecules are immobilized by being entrapped in the sol-gel. In one case, horse-heart cytochrome c was encapsulated in a sol-gel and absorbance-based spectral shifts were used to monitor the binding of nitric oxide. See Blyth et al., "Sol-Gel Encapsulation of Metalloproteins for the Development of Optical Biosensors for Nitrogen Monoxide and Carbon Monoxide" *Analyst* 120:2725 (1995). Unfortunately, the sensor reaction is reported to have taken two hours to reverse, making dynamic measurements impossible.

What is needed is a sensor of relatively small size and good sensitivity that measures nitric oxide with little or no interference from other analytes in a short enough time period to permit dynamic measurements.

SUMMARY OF THE INVENTION

The invention relates generally to optical sensors, methods of sensor fabrication and uses of such sensors, and more particularly the use of such sensors for the detection if nitric oxide. The present invention contemplates both fiber-optic sensors and optical fiberless sensors comprising nitric oxide-binding compounds, such compounds permitting the specific binding of nitric oxide (e.g., non-covalent binding) with little or no interference from other analytes.

A. Fiber-optic Sensors With Binding Compounds

With regard to fiber-optic sensors, the present invention contemplates an optical fiber having a fiber tip, said tip comprising an immobilized nitric oxide-binding compound. It is not intended that the present invention be limited by the means by which the nitric oxide-binding compound is immobilized. In one embodiment, the tip of the fiber is treated so as to have reactive groups and the nitric oxide-binding compound is covalently linked directly to the fiber via the reactive groups. In another embodiment, the tip has an inert coating (i.e., inert relative to nitric oxide) such as a metal layer (preferably, a non-linear layer and more preferably, spheres comprising metal) and the nitric oxide-binding compound is immobilized on the metal layer. In a preferred embodiment, the tip is treated to create reactive groups (e.g., thiol groups), spheres of metal colloid are attached to the tip via the reactive groups, and the nitric oxide-binding compound is immobilized on the metal colloid spheres.

It is not intended that the present invention be limited to the nature or dimensions of the metal layer. A variety of metals and metal colloids are contemplated, including but not limited to, colloids of gold, silver, tungsten, thoriasol, antimony pentoxide, carbon, red iron oxide, titanium dioxide and platinum (available commercially from Vector Laboratories, Inc., Burlingame, Calif.; Nanoprobes, Inc., Stony Brook, N.Y.; and Polysciences, Inc., Warrington, Pa.). In a preferred embodiment, the metal layer is a monolayer of spheres comprising gold colloid, said spheres attached to an end of a fiber as a substrate for spontaneous attachment of the nitric-oxide-binding compound. While not limited to particular dimensions, the size of the gold colloid does produce a marked difference in the fluorescence intensity measured. The present invention contemplates colloid sizes (and in particular gold colloid sizes) ranging from very small, 2 nm, to very large, 250 nm (and more preferably, between 5 nm and 100 nm), said colloids immobilized on the end of a fiber to provide a base for protein attachment. While a precise understanding of the mechanism for this phenomenon is not necessary in order to practice the invention, it is surmised the intensity changes seen in the fluorescence emission are not a result of surface coverage, and availability of sites for protein adsorption, but instead a quenching or enhancement by the gold itself. In general, the optimum fluorescence is achieved with particles sizes of approximately 100 nm.

In another embodiment, the nitric oxide-binding compound is a porphyrin group- or heme group-containing protein. In another embodiment, the nitric oxide-binding compound is a heme-binding protein. Regardless of whether the protein is a heme-group-containing protein or a heme-binding protein, in one embodiment, the present invention contemplates that the protein (or peptide) is dye-labeled (e.g., with dyes which can be used for protein labeling that do not react to nitric oxide, such as Oregon Green dyes). This has been found to increase the signal to noise ratio of the sensors of the present invention.

It is not intended that the present invention be limited to specific heme-group-containing proteins. The heme-group-containing proteins are limited only in the respect that they bind nitric oxide, and more preferably, they bind nitric oxide specifically (i.e., they do not bind interfering substances). The preferred heme-group-containing protein is cytochrome c' (as distinct from cytochrome c). It is not intended that the present invention be limited to the source of cytochrome c'. Nonetheless, preferred sources include, but are not limited to, microorganisms, more preferably bacterial sources, and more particularly, purple phototropic bacteria, aerobic nitrogen-fixing bacteria, and facultatively denitrifying bacteria, and still more particularly, sources such as *C. vinosum*, *R. purpureus*, and *R. gelatinosa*.

Insects have been shown to have both heme group-containing proteins that bind nitric oxide (M. C. Ribeiro et al., "Reversible Binding of Nitric Oxide by a Salivary Heme Protein from a Bloodsucking Insect," *Science* 260:539 (1993); J. G. Valenzuela et al., "A Salivary Nitrophorin (Nitric-Oxide-Carrying Hemoprotein) In The Bedbug Cimex lectularius," *J. Exper. Biol.* 198:1519 (1995)], as well as heme-binding proteins [P. L. Oliveira et al., "A Heme-binding Protein from Hemolymph and Oocytes of the Blood-sucking Insect, *Rhodnius prolixus*," *J. Biol. Chem.* 270:10897 (1995)]. The present invention contemplates both groups of proteins as useful in the preparation of optical sensors.

It is not intended that the present invention be limited to specific heme-binding proteins. The heme-binding proteins are limited only in the respect that they bind nitric oxide, and more preferably, they bind nitric oxide specifically (i.e., they do not bind interfering substances). The preferred heme-binding protein is the heme-binding protein isolated and characterized from both the hemolymph and oocytes of the blood-sucking insect, *Rhodnius prolixus*.

B. Fiber-optic Sensors With Attached Dyes

The present invention also contemplates sensors without binding compounds. More specifically, the present invention contemplates a sensor based on analyte adsorption to a metal surface reported by fluorescence changes of an attached dye molecule. It is also not intended that the present invention be limited by the nature of the particular dye. In one embodiment, said dye is a fluorescein or fluorescein derivative adsorbed to a metal (e.g. gold) surface. In another embodiment, diaminofluorescein is adsorbed to a gold surface. In a preferred embodiment, difluorofluorescein is adsorbed onto a gold surface.

C. Fiberless Sensors With Binding Compounds

The invention also contemplates optical fiberless sensors capable of detecting nitric oxide. The sensors of the present invention are: (1) small enough to enter a single mammalian cell relatively non-invasively, (2) fast and sensitive enough to catch even minor alterations in the concentration of nitric oxide and (3) mechanically stable enough to withstand the manipulation of the sensor to specific locations within the cell. Importantly, the fiberless sensors of the present invention are non-toxic and permit the simultaneous monitoring of several cellular processes.

In one embodiment, the present invention contemplates fiberless optical sensors comprising a nitric oxide-binding compound. It is not intended that the present invention be limited by the precise composition of the fiberless sensors. The fiberless sensors of the present invention are either solid or semisolid particles ranging in size between approximately 1 micrometer and 1 nanometer in diameter, and more preferably, between 5 nanometers and 250 nanometers. The ultimate small size is attained by fine grinding and filtering or by micro-emulsion techniques used to form mono-disperse colloidal particles (rather than nano-fabrication). In one embodiment, the sensor is selected from the group consisting of polymer fiberless sensors, acrylamide fiberless sensors, sol-gel fiberless sensors and metal fiberless sensors.

In one embodiment, the polymer fiberless sensors of the present invention comprise a nitric oxide-binding compound (such as a porphyrin) and a polymer. It is not intended that the present invention be limited to a particular polymer. In one embodiment, the polymer is selected from the group consisting of poly(vinyl chloride), poly(vinyl chloride) carboxylated and poly(vinyl chloride-co-vinyl acetate-co-vinyl alcohol). In a particular embodiment, the polymer fiberless sensors further comprise an additive and a plasticizer.

In one embodiment, the acrylamide fiberless sensors of the present invention comprise polyacrylamide and a nitric oxide-binding compound. In a preferred embodiment, the acrylamide fiberless sensors further comprise N,N-methylenebi-(acrylamide) and the mixture is polymerized to a gel.

In one embodiment, the sol-gel fiberless sensors of the present invention comprise a nitric oxide-binding compound entrapped in a matrix, such as a silica sol. Where the compound is a protein, stabilizers can be used. The gels are typically aged before use.

In one embodiment, the metal fiberless sensors of the present invention comprise a nitric oxide-binding protein (or peptide) in combination with a metal selected from the group consisting of gold, silver, platinum and alloys thereof (e.g., a gold/silver alloy). In one embodiment, the protein (or peptide) is dye-labeled (e.g, with Oregon green 514). Typically, such metal fiberless sensors are made by combining between 0.01% and 1%, and more preferably approximately 0.1% protein or peptide (by weight) in colloid solution. Spontaneous adsorption of the protein to the metal surface takes place within minutes.

D. Fiberless Sensors With Attached Dyes

The present invention also contemplates fiberless sensors with attached dyes, including but not limited to metal fiberless sensors. In one embodiment, the metal fiberless sensors of the present invention comprise a fluorescein derivative dye attached to colloidal gold. It is not intended that the present invention be limited by the type of fluorescein derivative dye. In one embodiment, said fluorescein derivative dye is 4-carboxy-2',7',-difluorofluorescein, succinimidyl ester. It is not intended that the present invention be limited by the geometry of the colloidal gold applied to the sensor tip. In one embodiment, said colloidal gold is 50 nm in thickness. It is not intended that the present invention be limited by the geometry or preparation of the metal fiberless sensor. In one example, said metal fiberless sensor are 100 $\mu$m core diameter multimedia fibers. In another example said sensors are prepared from 0.5×4.5 cm$^2$ quartz slides.

In one embodiment, said metal fiberless sensors of the present invention comprising a fluorescein derivative dye attached to colloidal gold are coupled with reference microspheres. It is not intended that the present invention be limited to the type of reference microsphere. In one embodiment, 40 nm fluorescent carboxylate-modified polystyrene microspheres with 488 nm excitation and 685 nm emission are coupled to the sensor tip.

It is not intended that the present invention be limited by the manner in which the sensors of the present invention are introduced into cells. In one embodiment, a buffered suspension of fiberless sensors is injected into the sample cell with a commercially-available pico-injector. In another embodiment, the fiberless sensors of the present invention are shot into a cell with a commercially-available particle delivery system or "gene gun" (such gene guns were developed and are now routinely used for inserting DNA into cells). In other embodiments, the fiberless sensors of the present invention are remotely steered into a cell, by photon pressure or "laser tweezers". This uses an infra-red laser beam which traps the particles or magnetically, by remotely steering magnetic nanoparticle pebbles (commercially available) into a cell.

It is also not intended that the present invention be limited by the detecting means. In one embodiment, the fiberless sensors of the present invention are addressed by laser beams (rather than fibers), and their fluorescent signals are collected and analyzed by procedures identical to those used for the fiber-tip nanosensors. See U.S. Pat. Nos. 5,361,314 and 5,627,922 to Kopelman et al., hereby incorporated by reference.

DEFINITIONS

Figure 1:
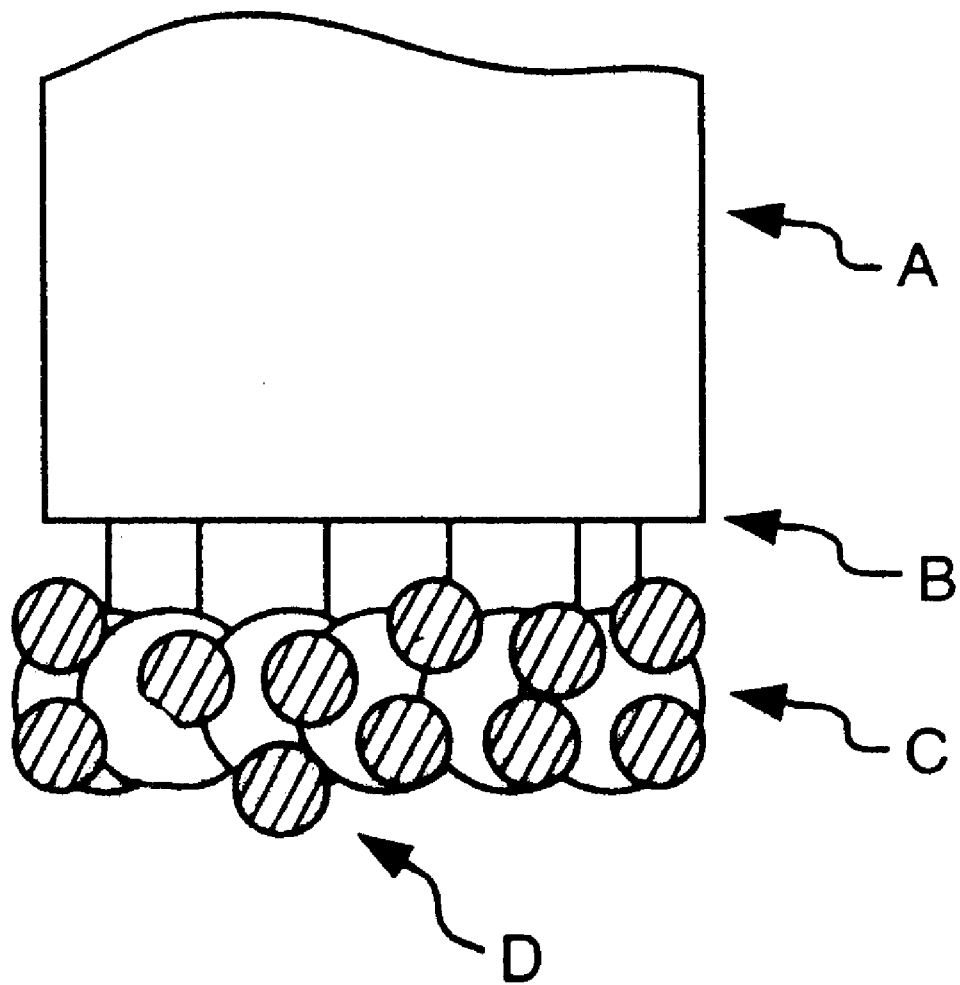
FIG. 1 schematically shows one embodiment of an optical fiber sensor of the present invention having a monolayer of metal spheres for attachment of a nitric oxide-binding protein.

To facilitate understanding of the invention, a number of terms are defined below.

The term "analyte" is intended to comprise any substance within a cell, including but not limited to nitric oxide and Na+, K+, Ca++, Cl−, H+, as well as oxygen and glucose.

The term "bacteria" refers to any bacterial species including eubacterial and archaebacterial species.

The term "chemical reaction" means reactions involving chemical reactants, such as inorganic compounds.

The present invention contemplates "metal conjugates" such as conjugate comprising a nitric oxide-binding compound attached to a metal, including but not limited to, metal in the form of a metal colloid.

Colloids are solutions of dispersed or suspended particles. Where the particles comprise metal, the colloid is referred to as a "metal colloid".

The present invention contemplates "porphyrin group-containing proteins" and more preferably "heme group-containing proteins" capable of binding (and more preferably, binding selectively) nitric oxide. The porphyrins are named and classified on the basis of their side chain substituents, such as etioporphyrins, mesoporphyrins, uroporphyrins, coproporphyrins and protoporphyrins. The chelate complex of a porphyrin (e.g., protoporphyrin) with metal is contemplated by the present invention as useful for nitric oxide binding. The chelate complex with iron [e.g., Fe(II), Fe(III)] is heme. Thus, the present invention specifically contemplates the use of ferrous and ferric hemoproteins to bind nitric oxide, and fragments thereof (preferably heme group containing fragments).

It is not intended that the present invention be limited by the type of porphyrin group-containing protein. In one embodiment, the present invention contemplates cyclases, including but not limited to, guanylate cyclase (which contains one protoporphyrin-IX type heme/heterodimer) and fragments thereof. See generally Stone and Marletta, "Soluble Guanylate Cyclase from Bovine Lung: Activation with Nitric Oxide and Carbon Monoxide and Spectral Characterization of the Ferrous and Ferric States," *Biochemistry* 33:5636 (1994). In another embodiment, the present invention contemplates ferrous hemoproteins such as hemoglobin and myoglobin, or fragments thereof. In still another embodiment, the present invention contemplates cytochromes or portions of cytochromes as nitric oxide binding compounds. In a preferred embodiment, the present invention contemplates cytochrome c' (as distinct from cytochrome c) and fragments thereof.

The present invention also contemplates compounds that bind porphyrins and heme. By the term "heme binding proteins" it is meant to indicate proteins that bind heme groups. It is not intended that the present invention be limited to particular heme group-binding proteins. In one embodiment, the heme-binding compound is the 93,000 molecular weight, heme-binding protein from rabbit serum. See Tsutsui and Mueller, *J. Biol. Chem.* 257, 3925 (1982). In another embodiment, the heme-binding protein is selected from the group consisting of globin, serum albumin, and transferrin. In yet another embodiment, the present invention contemplates the heme-binding protein isolated and characterized from both the hemolymph and oocytes of the blood-sucking insect, *Rhodnius prolixus*.

A compound is "immobilized" by attachment (whether covalent or non-covalent) or by encapsulation (e.g., in a gel such as a sol-gel).

In one embodiment, the present invention contemplates that the nitric oxide-binding compound is a protein (or peptide) and the protein (or peptide) is dye-labeled. There are three major classes of commonly used reagents to label amines: succinimidyl esters, isothiocyanates and sulfonyl chlorides. Dyes containing such groups are commercially available from Molecular Probes, Inc. (Eugene, Oreg.) and include, but are not limited to, such fluorophores as cascade blue, isosulfan blue, fluorescein, naphthofluorescein, malachite green and Oregon green).

A "fluorescent reference compound" is a compound that provides for a ratiometric measurement where the ratio (R) is calculated as the ratio of fluorescence intensity of a fluorescent reporter dye to the fluorescence intensity of the fluoresent reference compound.

A "fluorescent microsphere" is one type of fluorescent reference compound. While it is not intended the present invention be limited to any specific fluorescent microsphere configuration or emission profile, in one embodiment said microspheres are 40 nm fluorescent carboxylate-modified polystyrene with 488 nm excitation and 685 nm emission.

As used herein "fragments" or "portions" of proteins are typically more than four amino acids in length. The present invention, in a preferred embodiment, contemplates "functional" fragments or portions (i.e. fragments or portions capable of binding). Such functional fragments are typically more than 20 amino acids in length.

A "fluorescein derivative" is a compound wherein the core fluorescein molecule has been derivatized to contain modified groups (e.g. fluorescein-5-carboxylic acid, fluorescein-6-carboxylic acid, fluorescein diacetate, diaminofluorescein, etc) or where it has been attached to another biomolecule (e.g. fluorescein-biotin).

"Initiating a reaction" means causing a reaction to take place. Reactions can be initiated by any means (e.g., heat, wavelengths of light, addition of a catalyst, etc.)

"Interfering substances" are those substances that interfere with the measurement of nitric oxide. Such substances include but are not limited to nitrite, dopamine, uric acid, ascorbic acid, and cysteine.

The term "microorganism" as used herein means an organism too small to be observed with the unaided eye and includes, but is not limited to bacteria, viruses, protozoans, fungi, and ciliates.

"Reactive groups" are those chemical groups that are capable of reacting with (and thereby capable of securing) compounds or substances to the fiber tip. Such groups include groups having a S, N or O functionality, including but not limited to thiol groups, carboxylic acids and amino groups.

A "solvent" is a liquid substance capable of dissolving or dispersing one or more other substances. It is not intended that the present invention be limited by the nature of the solvent used.

A "fluorescence lifetime-based biosensor", as used herein, refers to a sensor incorporating a nitric oxide binding compound (e.g. cytochrome c') labeled with a fluorescent reporter dye wherein changes in said dye's intensity or fluorescence lifetime are observed as a function of nitric oxide binding. Nanosecond electronic state fluorescence lifetimes can be measured using a variety of techniques, including time-correlated single-photon counting.

DESCRIPTION OF THE INVENTION

The invention relates generally to optical sensors, methods of sensor fabrication and uses of such sensors, and more particularly the use of such sensors for the detection if nitric oxide. The present invention contemplates both fiber-optic sensors and optical fiberless sensors comprising nitric oxide binding compounds, such compounds permitting the specific binding of nitric oxide with little or no interference from other analytes. This nitric oxide sensors of the present invention are small (100 μm and submicrometer), very selective and can be used for dynamic, real-time measurements.

A. Fiber-Optic Sensors and Their Fabrication

Micro-fiberoptic sensors (100–1000 mn) are based on optical grade silica fibers pulled to submicron size. The pulled fiber tips are much less fragile than those of the electrochemical microsensors, which are made from pulled micropipettes. Traditionally, a dye-polymer matrix is attached to the tip, which is very durable and smooth and runs tightly bound to the tip, even during penetration of biological tissues. The matrix on the end of the fiber often includes several components, such as a chromoionophore, an ionophore, and appropriate ionic additives, all trapped inside a polymer layer, so that no chemicals are free to diffuse throughout the cell. The effects of toxicity of the dyes are thus minimized. Also, the probe can be carefully positioned in the cell, allowing any specific area to be imaged or monitored.

The nitric oxide detecting sensors of the present invention, by contrast, has a metal monolayer attached to the tip. The fabrication involves treatment of the fiber so as to add reactive groups. Thereafter, the metal monolayer is attached, followed by immobilization of the nitric oxide-binding protein (see FIG. 1, where the fiber (A), the reactive groups (B), the metal monolayer (C) and the attached protein (D) are shown).

B. Optical Fiberless Sensors and Their Fabrication

The present invention contemplates nitric oxide detecting sensors that are fiberless sensors or Probes Encapsulated By BioListic Embedding (PEBBLEs). While a variety of such fiberless sensors are contemplated, the preferred fiberless sensors of the present invention are those made with metal particles, and in particular, metal colloids.

The fiberless sensors are particularly suitable for chemical analysis in mammalian cells, by inserting the sensors into the cell, and monitoring remotely. The sensor particles or beads can be dispersed in buffer solution and pico-injected into a cell. The particles can be monitored singly, in groups located at different positions, or several different kinds can be injected for simultaneous measurements of several distinct intracellular ion or small molecule concentrations.

The fiberless sensors of the present invention are prepared by coating metal (e.g., Au) colloids with a nitric oxide binding compound (e.g., cytochrome c') or a dye-labeled nitric oxide-binding compound. For some cellular applications, a phospholipid layer is added to the fiberless sensors contemplated by the present invention.

C. Uses of the Present Invention

The invention will be useful for, among other things, in the identification of cellular and subcellular responses which lead to disease. The fields in which the optical sensors of the present invention will find application are vast, and include basic research, diagnosis, and treatment of disease. Direct benefits to humans and the environment include the development of new drugs, understanding the synergistic response to complex mixtures of pollutants, and prevention of developmental and degenerative disorders.

As noted above, nitric oxide is emerging as one of the main neurotransmitters in the central and peripheral nervous systems. Accurate detection and measurement of nitric oxide in cells may be used diagnostically, given the role of nitric oxide in AIDS dementia, Parkinson's and Huntington's diseases.

1. Metal Colloids on Optical Fibers

While the nitric oxide detection features of the present invention have been underscored, the present invention brings elements that can be used more generically if desired. Specifically, the use of metal colloids on optical fibers can be used to bind proteins other than nitric oxide binding proteins.

For example, an environmentally sensitive probe can be prepared using a metal layer (e.g., gold colloid) on the fiber tip. A dye can be attached to the end of a fiber through a non-fluorescent protein (such as bovine serum albumin) and used as an indicator of the hydrophobicity of differing regions of a cell. All that has to be done is to use a dye which can easily be attached to a protein, and which is sensitive to changes in environment. Alternatively, any protein or peptide (such as a zinc finger peptide) which is sensitive to environmental changes or selectively binds certain analytes (such as $Zn^{2+}$) can be used. Such proteins/peptides may be naturally fluorescent or labeled with fluorescent dyes.

Attaching dyes to proteins can also be a useful method for measuring analytes in general.

Thus, the present invention contemplates fiber-optic sensors comprising an optical fiber having a fiber tip, said tip comprising an immobilized protein and a dye. The protein can be any protein that is inert (i.e., inert relative to analyte sought to be detected). The protein can be immobilized using a metal layer (preferably, a non-linear layer and more preferably, spheres comprising metal). In one embodiment, the tip of the fiber is treated so as to have reactive groups and the spheres of metal colloid are attached to the tip via the reactive groups. In this latter embodiment, a fiber tip/reactive group/metal colloid/immobilized protein/selective dye complex is created.

2. Fiberless Sensors Comprising Metal Particles

As noted above, the nitric oxide detection features of the fiberless sensors of the present invention have been underscored. However, it is contemplated that fiberless sensors of the present invention can be used to measure any alteration in any endogenous analytes of any cell. The present invention specifically contemplates transcutaneous monitoring (e.g., ear, skin) as well as continuous flow monitoring of cells in culture, organotypic culture, organ slices, isolated perfused organs, organs in situ, and whole animal monitoring.

The present invention contemplates that the fiberless sensors of the present invention can be used as diagnostic tools for earlier intervention (i.e., earlier than currently available) and treatment of disease.

In one embodiment, the metal fiberless sensors of the present invention comprise a protein (or peptide) conjugated to a metal such as a metal colloid. The protein can be any protein that is inert (i.e., inert relative to analyte sought to be detected), and linked to a dye. Alternatively, any protein or peptide which is sensitive to environmental changes or selectively binds certain analytes (such as $Zn^{2+}$) can be used. Such proteins/peptides may be naturally fluorescent or labeled with fluorescent dyes. The protein can be immobilized using metal particles (preferably, a non-linear and more preferably, spheres comprising metal). In this latter embodiment, a metal colloid spherical particle/immobilized protein/selective dye complex is created.

D. Gases and Solutions

In some embodiments of the present invention, $K_2HPO_4$ and $KH_2PO_4$ were utilized to prepare 100 mM and 1 M pH 7.4 buffers. Peroxynitrite solutions were produced by dissolving $NH_4ONOO$ in 1.039 N KOH at 0° C., or according to a procedure adapted from that of Hughes and Nicklin which involved mixing 50 mM $NaNO_2$ with 50 mM $H_2O_2$ at 0° C. in the presence of 0.977 N HCl and quenching the reaction rapidly with 1.039 N KOH. The above referenced reagents are available from commercial sources such as Aldrich and Calbiochem. The concentration of peroxynitrite produced was determined by absorbance measured at 302 nm. Superoxide was produced from the reaction of oxygen with 45 mM ferrous sulfate. The absorbance (550 nm) of 80 $\mu$M cytochrome c was used to determine the concentration of superoxide. All solutions were prepared with 18-MΩ water, Barnstead I Thermolyne Nanopure II system (Dubuque, Iowa).

In addition, substantially pure (i.e., 99.998%, Matheson) $O_2$ and NO are available from Cryogenics.

E. Apparatus for Evaluating Fluorescence and Absorbance Spectroscopies

In one embodiment the sensor excitation source used to measure fluorescence and absorbance spectroscopies is a 488 nm Ar+ laser operating at 40 mW (Ion Laser Technology) with a neutral density filter, O.D.=1.0. The laser light was coupled into the fiber using a Newport fiber coupler. Sensor fluorescence spectra were collected through the optics of an Olympus inverted microscope and sent to an Acton Research Corporation spectrograph. The detector was a liquid nitrogen-cooled charge coupled device (CCD) from Princeton Instruments interfaced with an DFI P166 computer. Response times were measured by incorporating a Wavetek function generator to control the shutter system. Spectra were collected every 0.25 sec. and each acquisition was 0.01 sec in duration. The response time for increasing nitric oxide was measured by adding an aliquot of saturated nitric oxide solution to the sample buffer, and the response time for decrease in nitric oxide were measured by adding more buffer to dilute the nitric oxide. Solution fluorescence and excitation spectra were measured with a Spex Jobin-Yvon Instruments S. A. Fluorolog 3 spectrofluorophotometer. Absorbance measurements were made with a Shimadzu UV-160U UV-visible spectrophotometer controlled by a DTK computer using UV-160 Plus software.

F. Optical Apparatus for Fluorescence Lifetime Measurements

In one embodiment, nanosecond electronic state fluorescence lifetimes were measured using time correlated single photon counting. The excitation source was a titanium-sapphire laser (Spectra Physics) operating at 920 nn and 82 MHz, pumped by an Ar+ laser (Spectra Physics). An LBO doubling crystal (Super Optronics) produced 460 nm light which passed through a pulse picker (Conoptics), reducing the frequency to 4.1 MHz. The beam was split with the minor fraction of the light focused on a reference photodiode and the majority of the beam passing through a vertical linear polarizer and focused onto the sample cuvette. Fluorescence was collected at a polarization of 54.7° from vertical through a 580 nm bandpass (10 nm bandwidth) filter and detected with a microchannel plate photomultiplier tube (Hamamatsu 38094-50). The detection electronics (EG&G Ortec) were set up in reverse—timing mode, and the data collection rate was held to less than 1% of the excitation rate in order to minimize short time bias. Data collection (EG&G Ortec) and analysis (Photon Technology International) software were run on a DFI P166 computer.

Figure 20:
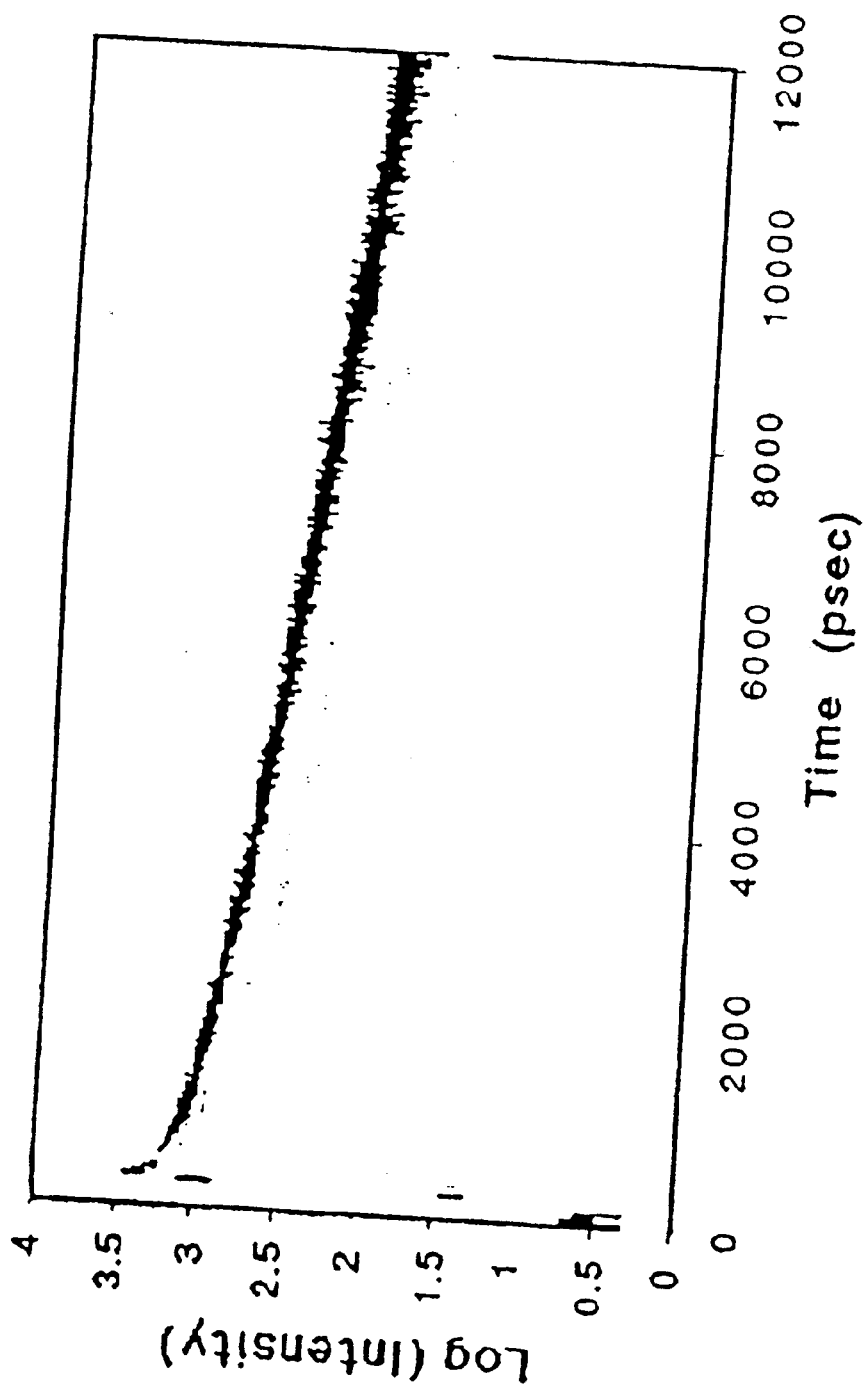
FIG. 20 presents time-domain fluorescence decay (at 580 nm) of dye-labeled cytochrome c' scrape-loaded into macrophages.

For example, a representative time-domain fluorescence decay (at 580 nm) of dye labeled cytochrome c' scrape-loaded into macrophages is presented at FIG. 20. Specifically, the black line represents the decay profile of untreated cells (with a fluorescence lifetime of 4.0 ns), wherein [NO]=0. The grey line (which is defined by the equation of a line substantially similar to said black line wherein said grey line is substantially contained in the area under said black line) represents the decay profile of macrophages treated with lipopolysaccharide (LPS) and recombinant mouse interferon-g (IFN-γ) (with a fluorescence lifetime of 3.5 ns), wherein [NO]=150 μM. The average intracellular nitric oxide concentration of macrophages activated with both LPS and IFN-γ was 160+/−10 M (average= 3.42+/−0.09). Cells activated with LPS and IFN-γ and inhibited with NMMA ($N^{\omega}$-monomethyl-L-arginine), were again used to verify the measure response was induced by nitric oxide.

G. Sensor Calibration

In one embodiment, sensor calibrations in the above referenced apparatus were made in 100 mM pH 7.4 phosphate buffer in a gas tight chamber with three stoppered ports. The sensor was placed through one septum and aliquots of saturated nitric oxide solution in 100 mM pH 7.4 phosphate buffer were injected through another with gas-tight syringes (VICI Precision Sampling, Inc.). The chamber was purged with nitrogen prior to calibration to avoid oxidation of the nitric oxide. The nitric oxide concentration was determined by dilution calculations from the 25° C. saturated solution concentration of 1.93 mM and verified as previously described. Due to the toxicity of nitric oxide, saturated nitric oxide solutions were prepared in a well-ventilated fume hood and sensor calibrations were performed in well-ventilated laboratory.

In another embodiment, sensor calibrations were made in 100 mM pH 7.4 phosphate buffer in a gas tight chamber with three stoppered ports (ratiometric fiber sensors) or a gas tight cuvette with a septum in the lid (lifetime measurements). The fiber sensors were placed through one septum of the chamber. For the lifetime measurements, a 0.7 (M solution of dye-labeled cytochrome c' in 100 mM pH 7.4 phosphate buffer was used. Aliquots of saturated nitric oxide solution in 100 mM pH 7.4 phosphate buffer were injected into the gas tight chamber or cuvette with gas-tight syringes (VICI Precision Sampling, Inc.). The chamber or cuvette, containing an initial volume of 100 mM pH 7.4 phosphate buffer, was purged with nitrogen prior to calibration to avoid oxidation of the nitric oxide. The nitric oxide concentration was determined by dilution calculations from the saturated solution concentration of 1.93 mM (25° C.) and verified as previously described.

H. Effects of Nitric Oxide on Gold-Adsorbed Flurophore

Figure 8:
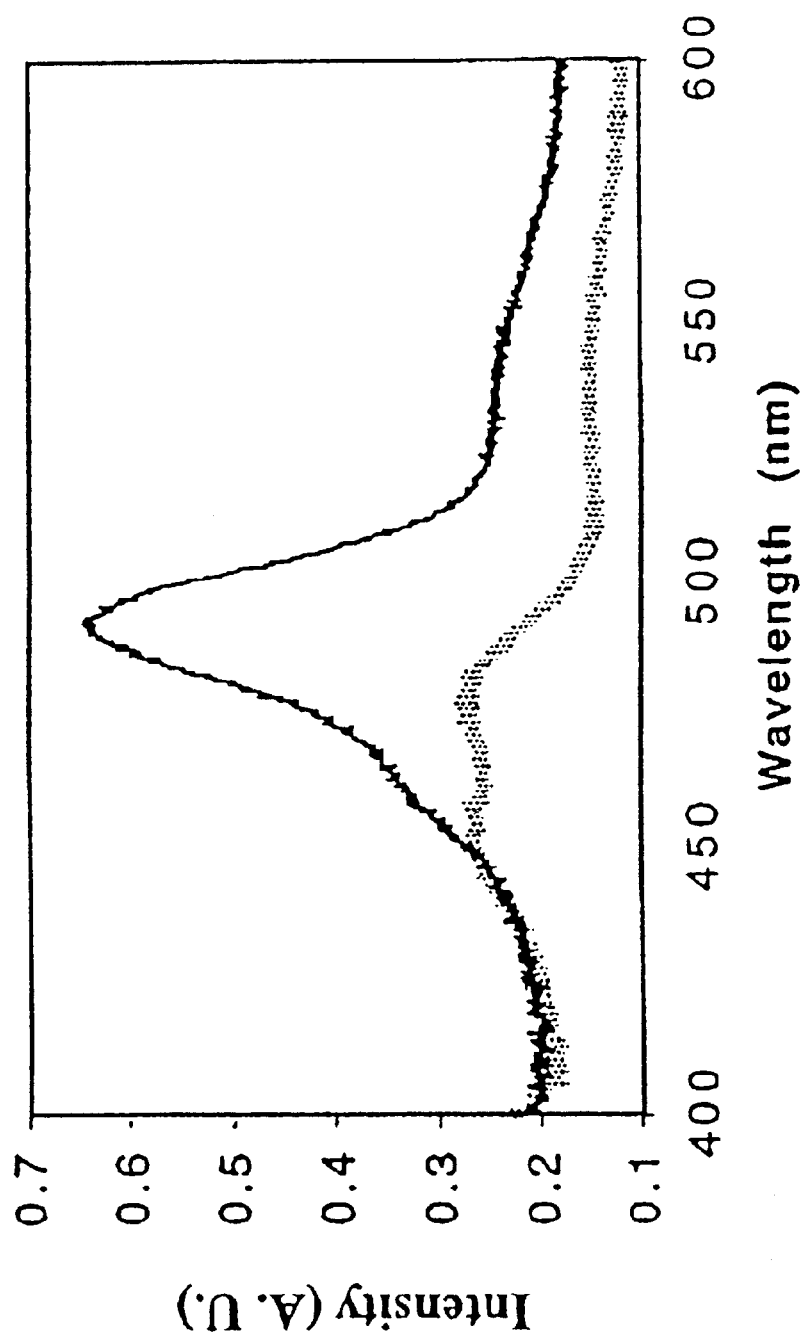
FIG. 8 presents the absorbance spectrum of a fluorescein derivative in a gold colloid solution wherein the solid line represents absorbance in a system purged with $N_2$ (wherein $[N_2]$ is substantially equivalent to atmosphere at sea level) and the dotted line represents absorbance in a system saturated with NO.
Figure 9:
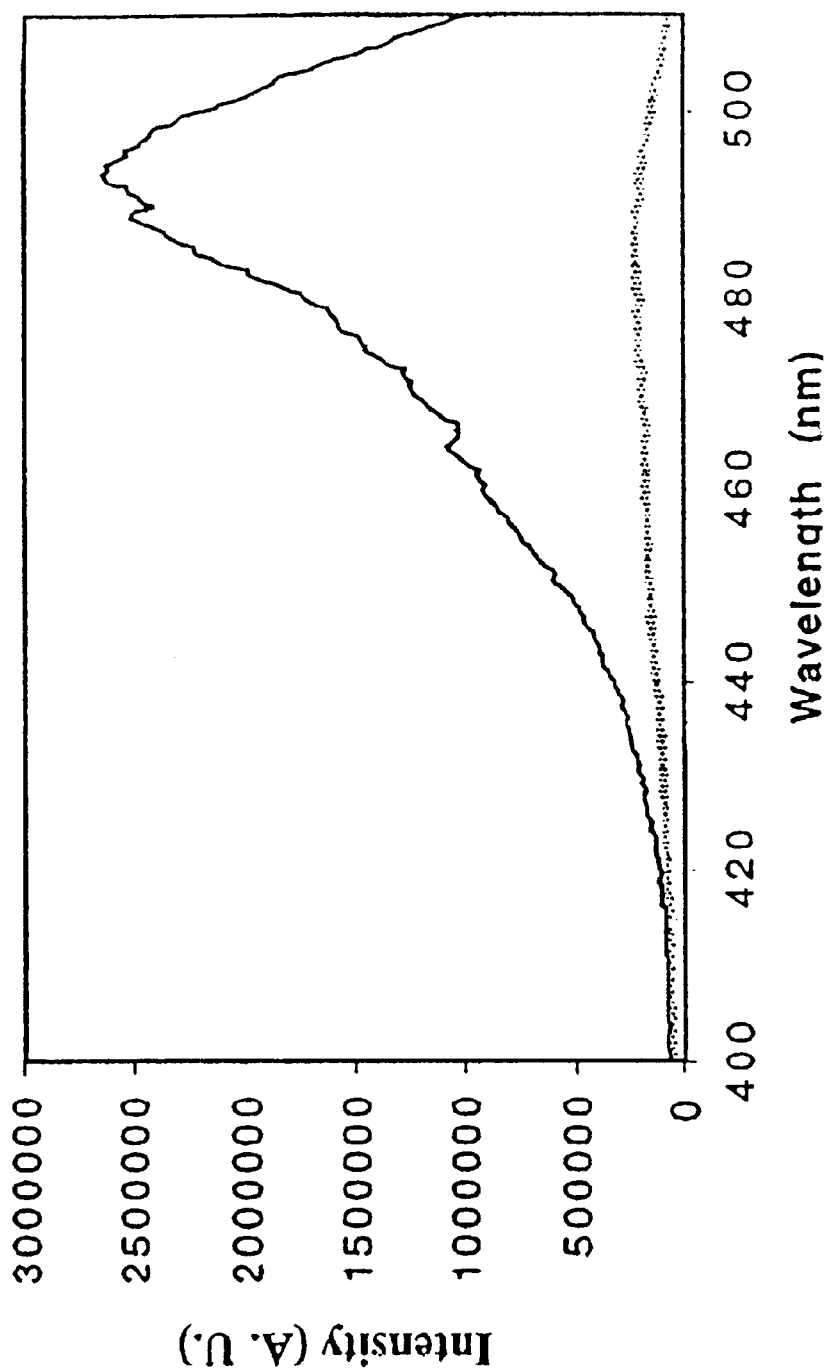
FIG. 9 presents the excitation spectrum of fluorescein derivative in a gold colloidal solution monitored at 517 nm wherein the solid line represents excitation in a system purged with $N_2$ (wherein $[N_2]$ is substantially equivalent to atmosphere at sea level) and the dotted line represents excitation in a system saturated with NO.
Figure 10:
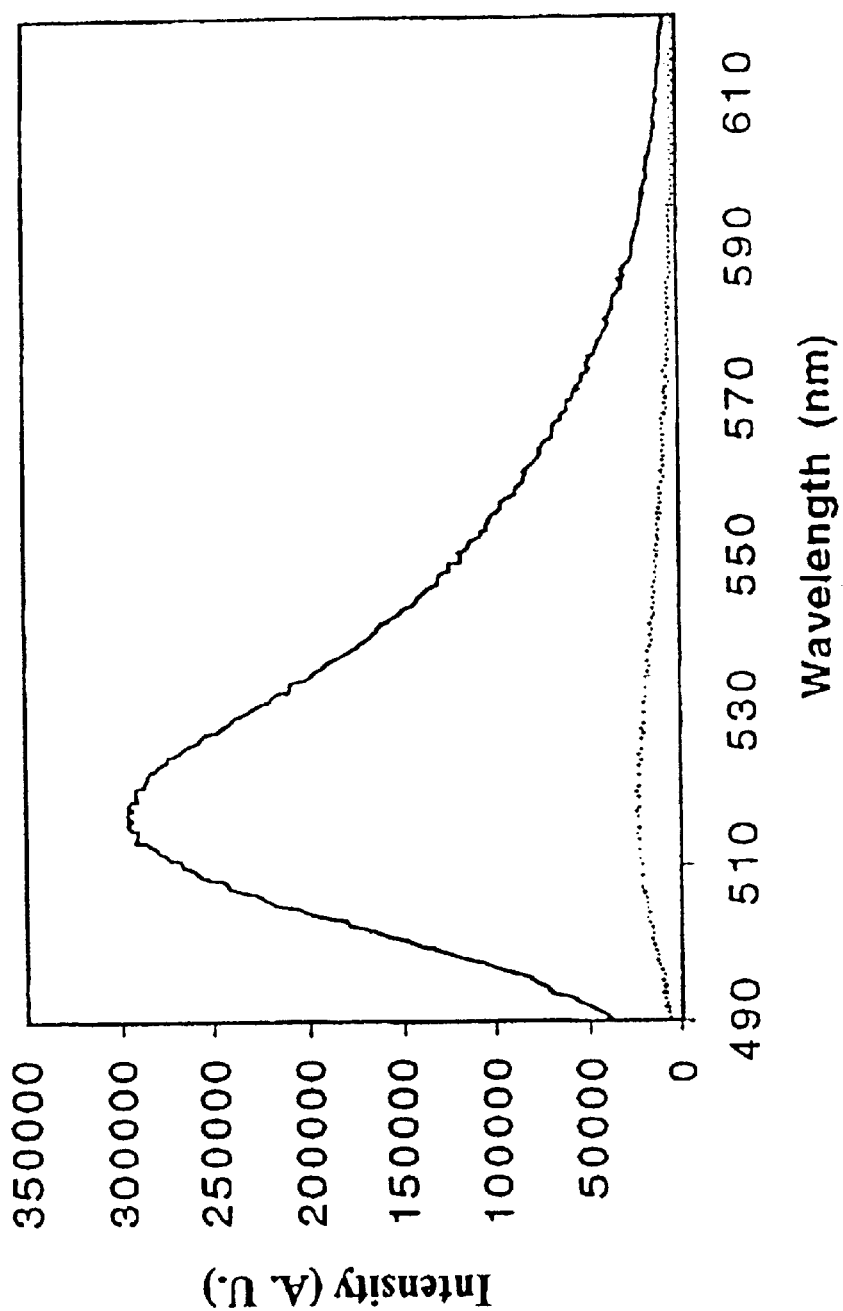
FIG. 10 presents the emission spectrum of fluorescein derivative in gold colloid solution excited at 488 nm wherein the solid line represents excitation in a system purged with $N_2$ (wherein $[N_2]$ is substantially equivalent to atmosphere at sea level)and the dotted line represents excitation in a system saturated with NO.
Figure 11:
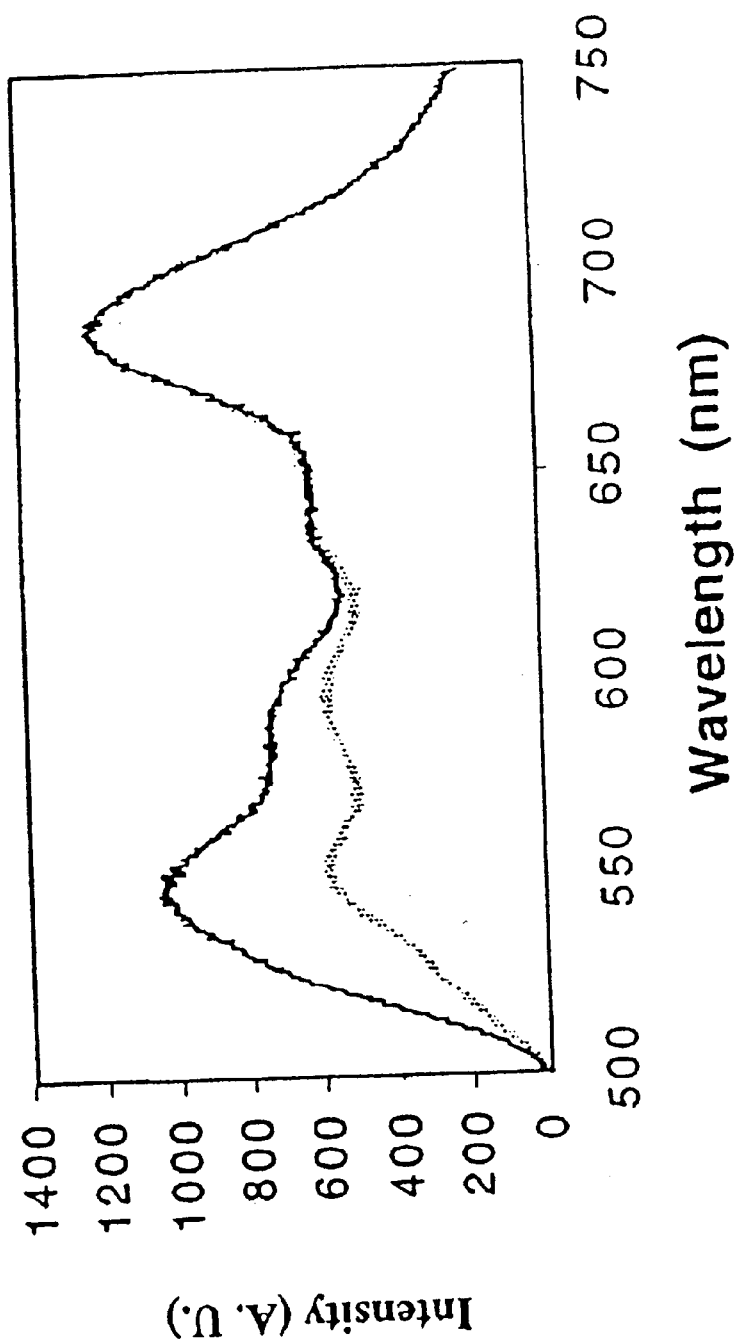
FIG. 11 presents the emission spectrum of one embodiment of an optical fiber sensor of the present invention, said fiber sensor having a fluorescein derivative dye attached to colloidal gold, excited at 488 nm wherein the solid line represents excitation in a system purged with $N_2$ (wherein $[N_2]$ is substantially equivalent to atmosphere at sea level) and the dotted line represents excitation in a system saturated with NO. It should be noted that the 685 nm peak corresponds to the fluorescence emission of the reference microspheres.

Dye absorbance, fluorescence excitation, and fluorescence emission show no spectral changes between difluorofluorescein derivative dyes in aqueous solutions purged with nitrogen and solutions saturated with nitric oxide. Dilute difluorofluorescein derivative dyes (0.2 mM) in a 50 nm colloidal gold solution (0.01%), however, do respond to nitric oxide. Specifically, the intensity decreases in the absorbance and fluorescence excitation and emission spectra upon addition of nitric oxide are shown in FIGS. 8–10. As observed in FIG. 11, a similar nitric oxide-induced decrease in fluorescence emission intensity was observed with fiber sensors prepared with a fluorescein derivative dye adsorbed onto a gold sensor tip.

Figure 12:
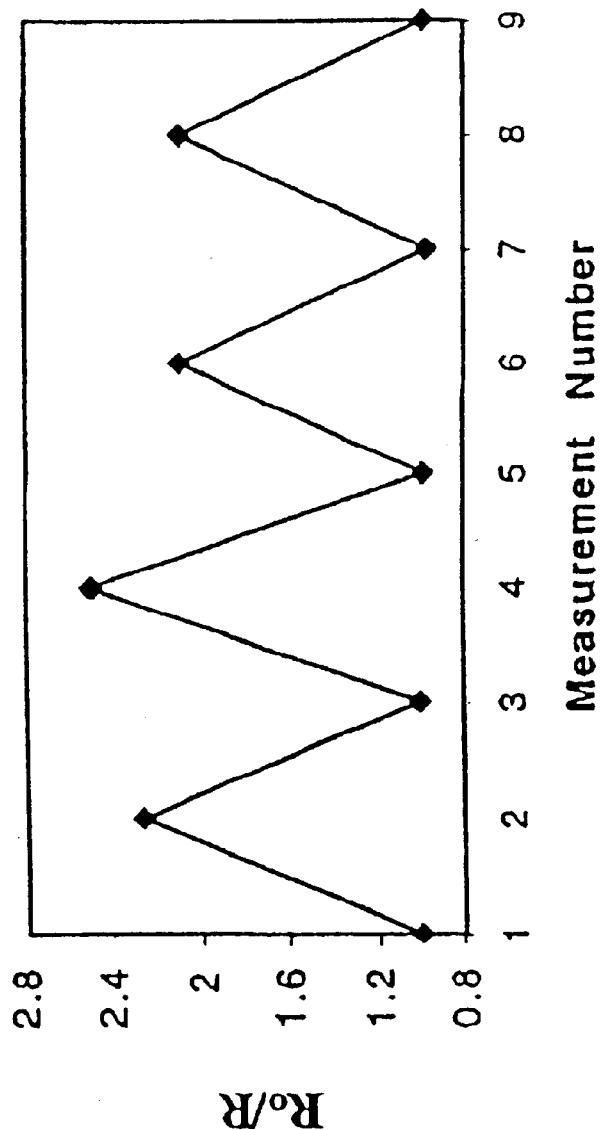
FIG. 12 presents data demonstrating the reversibility of an optical fiber sensor of the present invention, said fiber sensor having a fluorescein derivative dye attached to colloidal gold, wherein $R_0/R$ is plotted where $R_0$ is the dye ratio at zero nitric oxide concentration and R is the dye ratio at each nitric oxide concentration.
Figure 13:
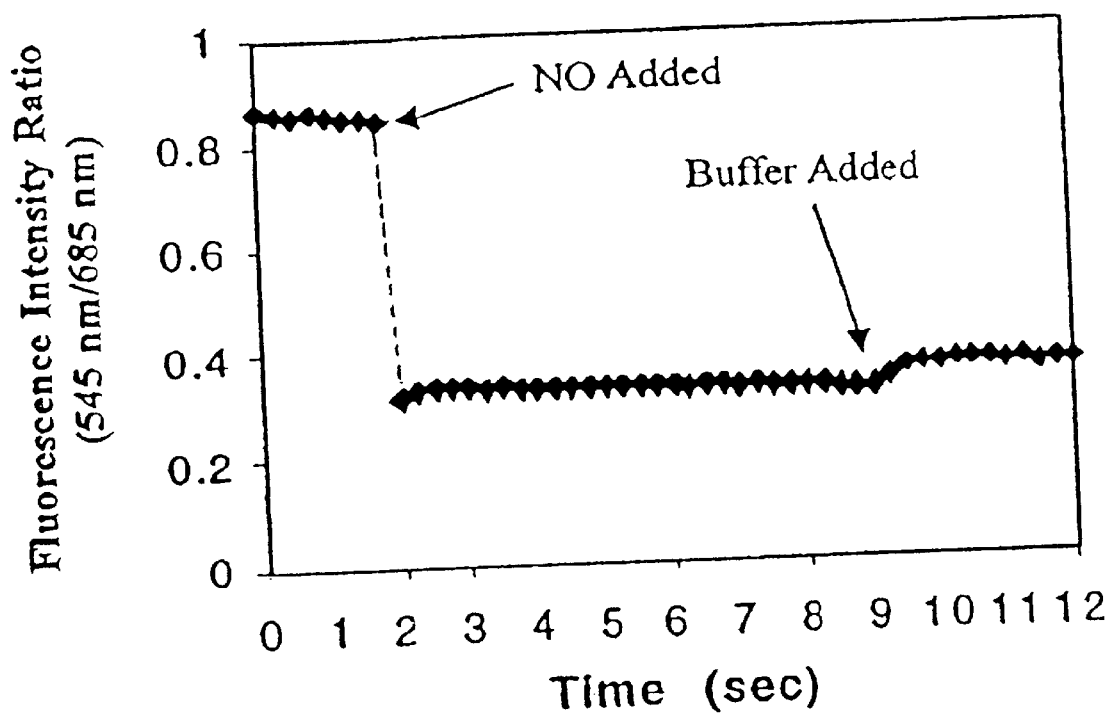
FIG. 13 presents the response time of fiber optic sensors where the ratio of fluorescence intensities is plotted versus time. The initial points are taken in 100 mM pH 7.4 phosphate buffer and qualitative aliquots of nitric oxide in 100 mM pH 7.4 and 100 mM pH 7.4 buffer are added sequentially.

Additionally, said fiber sensors prepared with a fluorescein derivative dye adsorbed onto a gold sensor tip demonstrate superior reversibility, as shown in FIG. 12. Moreover, said sensors have fast response times to increasing or decreasing nitric oxide, as demonstrated by FIG. 13. Indeed, the response time (0–100%) was measured to be 0.25 seconds or less. Said fiber sensors prepared with a fluorescein derivative dye adsorbed onto a gold sensor tip susceptibility to potential interferents has been evaluated, as shown in Table 1.

While it is not intended that the present invention be limited to any particular application, said fiber sensors prepared with a fluorescein derivative dye adsorbed onto a gold sensor tip have been utilized to measure the nitric oxide released by macrophages as shown in Table 2. Specifically, said sensors were placed in solution, approximately 0.5 cm from the macrophages. The inactivated cells produced nitric oxide levels below the sensor limit of detection. However, macrophages activated with both LPS and IFN-γ produced an average nitric oxide concentration of 190±70 mM. Activated macrophages produce nitric oxide, superoxide, and hydrogen peroxide.

I. Ratiometric Sensors

The present invention also contemplates the use of ratiometric sensors. In one embodiment, fluorescent microspheres (nonreactive to at least millimolar nitric oxide levels) were incorporated into the fiber optic sensors. The addition of said microspheres provide for ratiometric measurements, where the ratio (R) was calculated as the ratio of fluorescence intensity of the fluorescein dye to the fluorescence intensity of the reference spheres. In embodiments of the present invention where fiber sensors prepared with a fluorescein derivative dye adsorbed onto a gold sensor tip, said sensors were measured in the range 0–1 mM nitric oxide as the ratio (R) of the fluorescence intensity of the fluorescein derivative to the fluorescence intensity of the reference micro-spheres. The resulting response was linear ($r^2=0.993$) with a slope of 0.23 $\Delta R_0 R^{-1} mM^{31~1}$ NO, where $R_0$ is the dye ratio at zero nitric oxide and R is the dye ratio at each nitric oxide concentration. The upper limit of sensors using said ratiometric detection is 20 mM nitric oxide.

Figure 14:
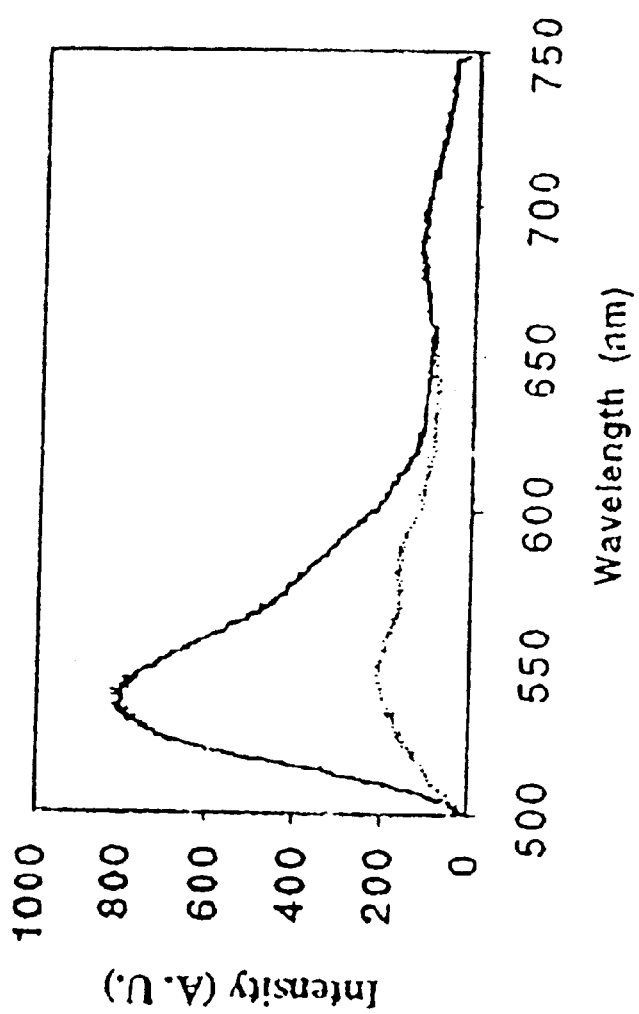
FIG. 14 presents emission spectra of an optical fiber sensor of the present invention, said fiber sensor having cytochrome c' labeled with a reporter dye, said dye-labeled cytochrome c' attached to said sensor via colloidal gold excited a 488 nm wherein the solid line represents the emission spectra in a system purged with $N_2$ (same concentration as air) and the dotted line represents excitation in a system saturated with NO. It should be noted that the 540 nm peak is the fluorescence emission of the dye-labeled cytochrome c' and the 685 nm peak is the fluorescence emission of the reference microspheres.

In another embodiment an optical fiber sensor, incorporating cytochrome c' linked to a labeling dye, were made ratiometric by the addition of a second fluorescent component, derivatized micro-spheres, which were added to the sensor tip. The 685 nm fluorescence of these spheres are nonreactive to at least millimolar concentrations of nitric oxide, making the emissions from said microspheres preferred as a reference peak. In one embodiment sensors incorporating the cytochrome c' labeling dye is modified, to utilize Oregon Green™ 488 carboxylic acid, succinimidyl ester. This embodiment enhances the simultaneous excitation with 488 rum light of the labeling dye and the reference spheres. The fluorescence emission spectrum from sensors incorporating Oregon Green™ 488 carboxylic acid, succinimidyl ester as a cytochrome c' labeling is presented in FIG. 14. In this embodiment, the sensor response was determined from the ratio (R) of fluorescence intensity of the labeling dye, Oregon Green™ 488, to the fluorescence intensity of the reference micro-spheres. Said sensors were calibrated over the range 0–0.7 mM nitric oxide and the response was found to be linear ($r^2=0.998$) with a slope of 0.56 $\Delta R_0^{-1} R^{-1}$ mM NO, where $R_0$ is the dye ratio at zero nitric oxide and R is the dye ratio at a given nitric oxide concentration. This slope is steeper than that previously reported for the dye-labeled cytochrome c' sensors, resulting in a lower limit of detection of about 8 $\mu$M (calculated from the smallest detectable signal that was at least three times larger than any signal fluctuations due to noise).

While it is not intended that the present invention be limited to any specific mechanism or sensor preparation protocol, the above referenced enhanced sensitivity was achieved by labeling the cytochrome c' with the Oregon Green™ 488 prior to protein adsorption to the fiber tip. This protocol results in signal contributions only from the dye on the cytochrome c', without influence of the dye adsorbed directly on the gold. Repeated calibrations with different sensors result in standard deviations on the order of 10 $\mu$M nitric oxide.

Figure 15:
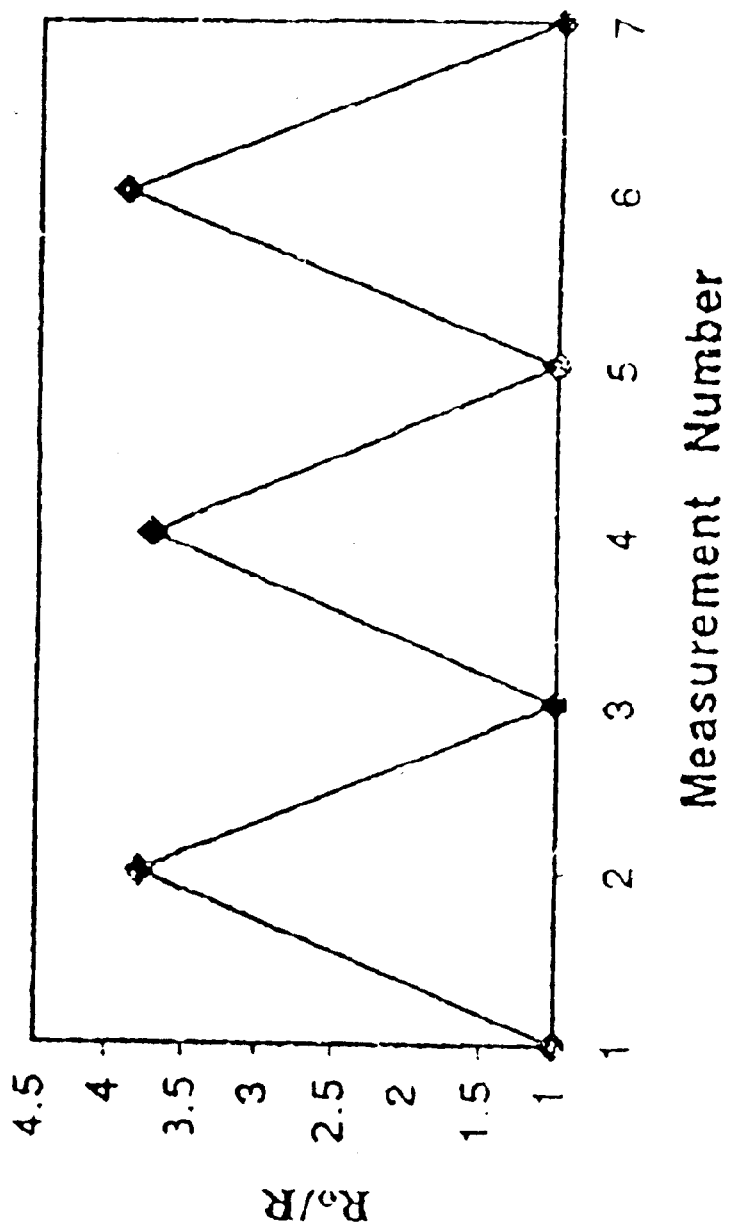
FIG. 15 presents data demonstrating the reversibility of an optical fiber sensor of the present invention, said fiber sensor having cytochrome c' labeled with a reporter dye, said dye-labeled cytochrome c' attached to said sensor via colloidal gold, wherein alternating measurements are presented in 100 mM pH 7.4 phosphate buffer and 100 mM phosphate buffer with high concentrations of nitric oxide.
Figure 16:
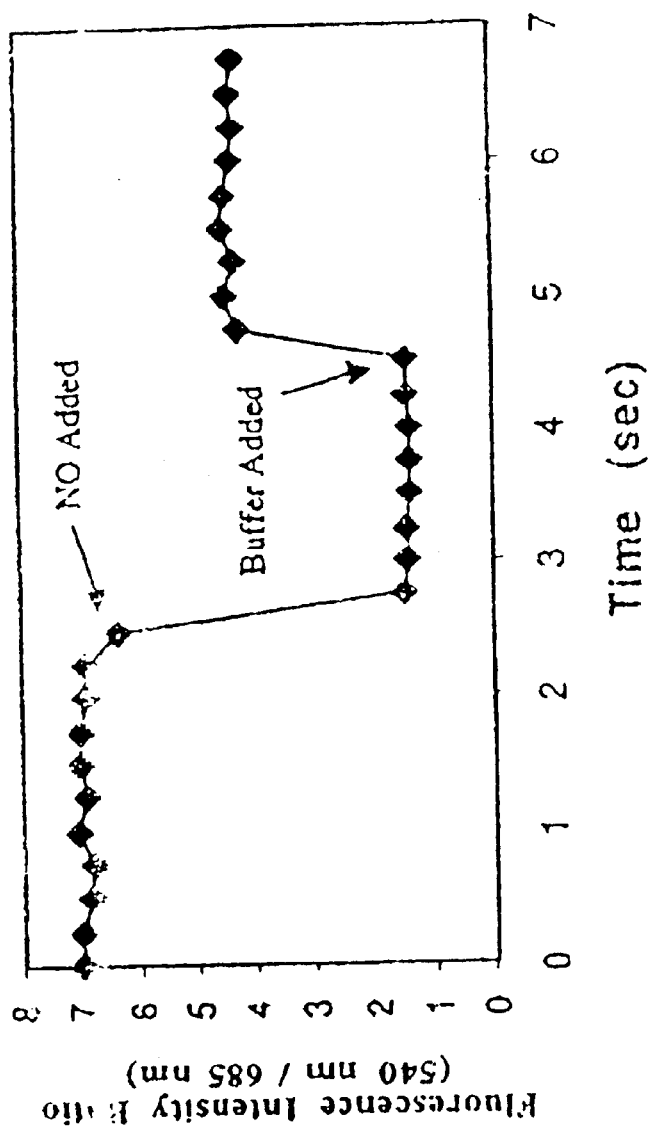
FIG. 16 presents data demonstrating the response time of an optical fiber sensor of the present invention, said fiber sensor having cytochrome c' labeled with a reporter dye, said dye-labeled cytochrome c' attached to said sensor via colloidal gold wherein initial points were taken in 100 mM pH 7.4 phosphate buffer, with qualitative aliquots of nitric oxide in 100 mM pH 7.4 and 100 mM pH buffer added sequentially.

In embodiments of the present invention incorporating cytochrome c' linked to a labeling dye made ratiometric by the addition of derivatized micro-spheres comprising a second fluorescent component, said micro-spheres demonstrate superior photostability and reversibility as presented in FIG. 15. In addition, embodiments of the present invention incorporating cytochrome c' linked to a labeling dye made ratiometric by the addition of derivatized micro-spheres comprising a second fluorescent component demonstrate superior response times to increases or decreases of nitric oxide as presented in FIG. 16.

In embodiments of the present invention incorporating cytochrome c' linked to a labeling dye made ratiometric by the addition of derivatized micro-spheres comprising a second fluorescent component the response to numerous potential interferents was determined. These sensors incorporating cytochrome c' linked to a labeling dye made ratiometric by the addition of derivatized micro-spheres comprising a second fluorescent component did not respond to 1M nitrite, 1 M nitrate, 1 M chloride, or 100% oxygen. Furthermore, the optimal pH range for said sensors is 6–9. Specifically, the labeling-dye fluorescence is sensitive to pH below 6, and the sensor signal decreases by 10–20% at pH 10–11. These sensors exhibited an average signal decrease of 8% in 6 $\mu$M superoxide.

J. Fluorescent Lifetime of Dye-labeled Cytochrome c'

Figure 17:
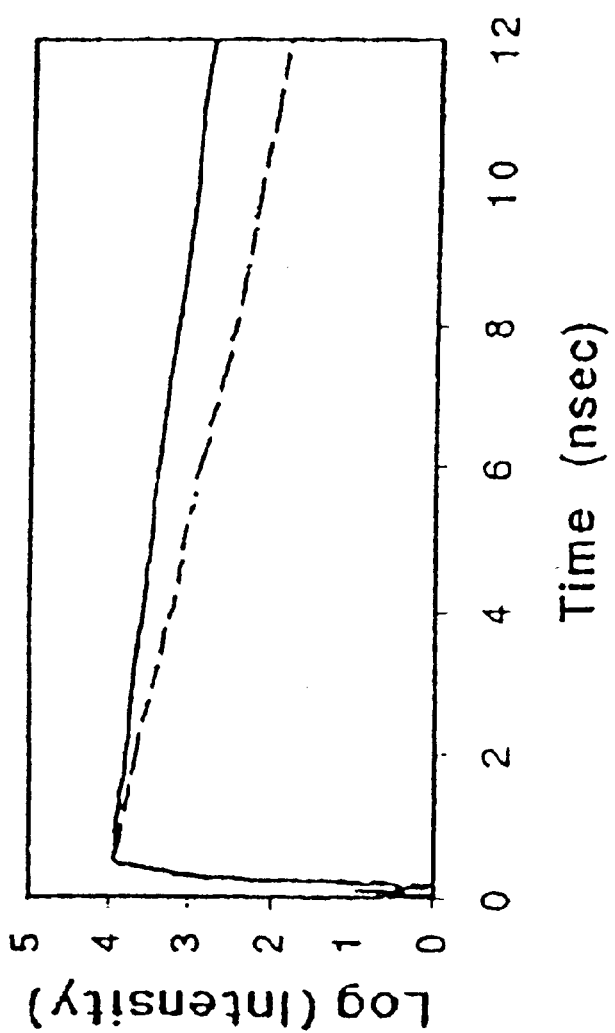
FIG. 17 presents data demonstrating fluorescence lifetime decay (at 580 nm) of dye-labeled cytochrome c' in 100 mM pH 7.4 solution wherein the solid line represents lifetime decay in 100 mM pH 7.4 phosphate buffer (4.0 ns) and the dashed line represents lifetime decay in 290 μM nitric oxide in 100 mM pH 7.4 phosphate buffer (3.0 ns).
Figure 18:
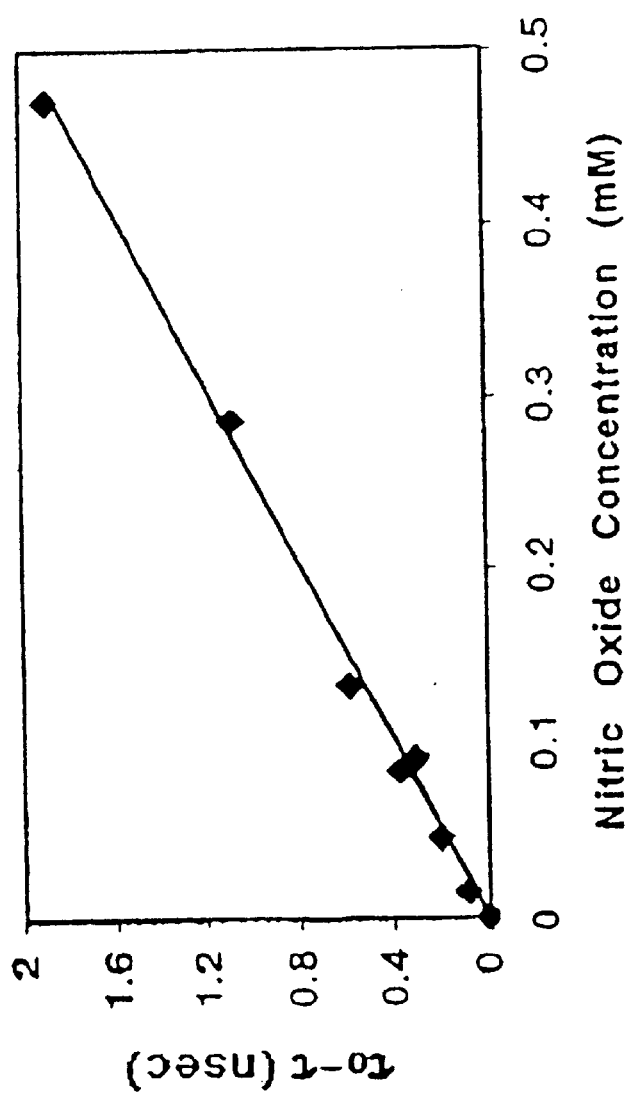
FIG. 18 presents calibration data (compiled from multiple calibrations) for fluorescence lifetime-based biosensor measurements wherein $\tau_0-\tau$ represents the difference between the fluorescence lifetime in the absence of nitric oxide ($\tau_0$) and fluorescence lifetime at each nitric oxide concentration ($\tau$).

In embodiments of the present invention incorporating cytochrome c' linked to a labeling dye made ratiometric by the addition of derivatized micro-spheres comprising a second fluorescent component, the fluorescence lifetime (t) of the dye-labeled cytochrome c' in 100 mM phosphate buffer solution was determined. While it is not intended that the present invention be limited by any specific florescent half life, the plot of fluorescence lifetime against nitric oxide concentration is presented in FIG. 17. Specifically, these fluorescent lifetimes were determined from an exponential fit of the long lifetime component of the fluorescence decay. When plotted as the difference ($t_0-t$) between the fluorescence lifetime in the absence of nitric oxide (to) and fluorescence lifetime at each nitric oxide concentration (t), the response was linear ($r^2=0.99$) with a slope of 3.9 $\Delta \tau$ (nsec)/mM NO and a limit of detection of 30 mM nitric oxide, as shown in FIG. 18.

K. Cell Culture

In one embodiment, the above referenced sensors were used to quantify nitric oxide production by macrophages derived from BALB/c mice. While it is not intended that the present invention be limited to any particular macrophage recovery technique, macrophages were derived from the femur bone marrow of Harlan Sprague-Dawley BALB/c mice were cultured and plated at a density of $2\times10^5$ on 25 mm coverslips by methods similar to previously published methods. Some macrophages were activated by overnight incubation with medium containing 100 U/mL IFN-γ enzyme Corp., Cambridge, Mass.) and 100 ng/mL LPS (List Biological Labs, Inc., Campbell, Calif.). In addition, to activation with IFN-γ and LPS, some cells were also treated with NMMA, (Sigma) to inhibit the production of nitric oxide. Prior to nitric oxide determinations, the macrophages were removed from incubation. For inactivated macrophages, the medium was exchanged for 2 mL Ringer's buffer. For activated macrophages, the medium was exchanged for 2 mL Ringer's buffer containing the same treatments as were found in the medium. During measurements, the cells were kept at ambient temperature (25° C.) and 7.5 mg/mL propidium iodide was used to ascertain the degree of cell viability.

In another embodiment, macrophages were derived from the tibia and femur bone marrow of Harlan Sprague-Dawley BALB/c mice were cultured and plated by methods similar to previously published methods. For extracellular measurements with fiber sensors the cells where plated at a density of $2 \times 10^5$ on 25 mm coverslips, while those to be used for scrape-loading were plated onto 35 mm petri dishes (Nunc) at a density of $2 \times 10^6$. Some macrophages were activated by overnight incubation with medium containing 100 μ/mL recombinant mouse interferon-g, IFN-γ, (Genzyme Corp., Cambridge, Mass.) and 100 ng/mL LPS. Some cells activated with IFN-γ and LPS were also inhibited with 1 mM NMMA (Sigma). Prior to nitric oxide determinations, the macrophages were removed from incubation. For extracellular measurements with optical fiber sensors, the medium was exchanged for Ringer's buffer. For untreated macrophages, the medium was exchanged for 2 mL Ringer's buffer. For activated macrophages, the medium was exchanged for 2 mL Ringer's buffer containing the same treatments as were found in the medium.

For intracellular lifetime-based sensor measurements, dye-labeled cytochrome c' in phosphate buffer (0.7 μM) was scrape-loaded into the cells, according to procedures well known in the art. The scrape-loaded cells were then re-plated onto 0.5×4.5 cm quartz slides, suitable for placement in a cuvette. Prior to measurements, the medium was exchanged for Ringer's buffer containing the same treatments as were found in the original medium. Micrographs of macrophages on coverslips were taken in a Zeiss Axioskop 2, using a Quantix cooled CCD camera (Photometrics). During measurements, the cells were kept at ambient temperature (25° C.). Cell viability was determined with 7.5 mg/mL propidium iodide.

L. Applications

Various fiber-optic tip sensors with fiberless ("pebble") sensors can be used. The fiber-optic nanotip fluorescent sensors are inserted into the cell by standard micropipette ("patch clamp") techniques. The chemical sensor nanotips and pebbles, with each tip or pebble specific to a given chemical analyte. Utilizing these optical nanosensors one can get a chemical video for a single analyte (say, calcium), analogous to a black and white movie, or of a list of chemical analyte (say, calcium, sodium, potassium, chloride, oxygen and pH), analogous to a color video or, alternatively, to six single color videos, each taken with a different narrow-band optical filter.

The cell is located under a microscope objective lens, and may be immobilized by a micopipette (standard technique). One or several fiber-optic nano-tips are inserted by fine manipulators. The fiber-optic tips may be multi-functional sensors (simultaneously measuring 2 or more analytes) and/or multiplexed fiber tips (simultaneously measuring 2 or more sensors). If sensor nanopebbles are inserted (via micropipette), they are addressed optically by laser beams, either directly or via optical fibers.

Elimination of cross-talk among the different nanosensors is based on a combination of spatial, temporal and spectral resolution. Different fiber-optic tip sensors are excited by different lasers or laser wavelengths. Image focusing on an intensified CCD (requested item) separates spatially the fluorescence from different nano-sensors. Spectral control of the excitation wavelength and spectral selection of the fluorescence wavelength separates the various signals.

Figure 19:
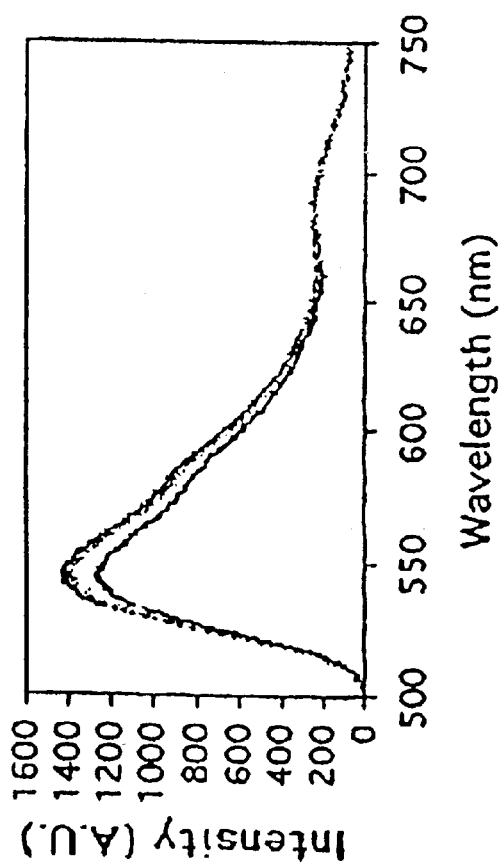
FIG. 19 presents fluorescence spectra data generated by an ratiometric optical fiber sensor of the present invention, said fiber sensor (made ratiometric with the addition of a second fluorescent component, derivatized micro-spheres, which have been added to the sensor tip having cytochrome c' labeled with a reporter dye) said dye-labeled cytochrome c' attached to said sensor via colloidal gold, of macrophage nitric oxide.

While it is not intended the present invention be limited to any specific application, in one embodiment the ratiometric sensors were used to measure the extracellular nitric oxide released by macrophages. See FIG. 19. In FIG. 19, the top black line presents the spectral profile of phosphate buffer ($R_0/R=1$, [NO]=0); while the bottom black line presents the spectral profile of macrophages treated with LPS and activated by overnight incubation with recombinant mouse interferon-γ (INF-γ), ($R_0/R=1.11$, [NO]=200 μM) and the gray line (which is substantially contained between said top black line and said bottom black line) tracts the area be presents the spectral profile of macrophages treated with LPS and INF-γ and inhibited with 1 mM $N^\omega$-monomethyl-L-arginine, ($R_0/R=1.01$, [NO]=20 μM). The sensors were placed in solution at approximately 0.5 cm from the macrophages. Nitric oxide levels were averaged over repeated measurements on multiple cell cultures. The untreated cells produced nitric oxide levels of less than 20 mM. Macrophages activated (to express inducible nitric oxide synthase) with a combination of LPS and IFN-γ, produced an average nitric oxide concentration of 210±90 mM.

The above results demonstrate the improved applicability of these ratiometric and lifetime-based cytochrome c' biosensors and their utility for cellular measurements. Such direct measurements provide for real time intracellular experimental analysis of nitric oxide. Indeed, direct microscopic measurements of individual cells will allow correlation of nitric oxide levels with various cellular activities. The methods described here indicate that such measurements are feasible and that extended applications of the sensors recited through the instant invention could provide valuable additional information about cellular nitric oxide.

EXPERIMENTAL

The following examples serve to illustrate certain preferred embodiments and aspects of the present invention and are not to be construed as limiting the scope thereof. In the experimental disclosure which follows, the following abbreviations apply: TEA (triethylamine; EDTA (ethylenediaminetetraacetic acid); IBMX (isobutylmethylxanthine); DTT (dithiothreitol; GTP (guanosine 5'-triphosphate); SNP (sodium nitroprusside).

EXAMPLE 1

In this example, sensors were prepared by silanizing a freshly cleaved multimedia fiber by immersing the distal end for two hours in 3-(mercatopropyl) trimethoxysilane, thereby modifying the fiber with reactive groups. The end was then rinsed copiously with methanol, then tripley distilled water. The silanized fiber was placed in colloidal gold (used as received from the manufacturer) for three hours, then rinsed with water. The sensor can be stored at this point in water or air.

Two protein solutions were prepared. The first solution was prepared by dissolving 0.1% r-phycoerythrin (Molecular Probes, Eugene, Oreg.) in phosphate buffer, pH 6.0. The fiber was then immersed in the protein solution for one hour, rinsed with buffer, then used.

A second protein solution was prepared by dissolving 0.1% bovine serum albumin (BSA) in phosphate buffer, pH 6.0. The fiber was then immersed in the protein solution for one hour, rinsed with buffer, then used. After BSA attachment, the fiber tip was placed in Texas Red-X (Molecular Probes, Eugene, Oreg.) solution for one hour. The dye solution was prepared by dissolving 1 mg Texas Red-X in dimethyl sulfoxide (DMSO) then adding 1 M sodium bicarbonate solution (pH 8.3). The sensor was rinsed with water before use.

The complete optical path for the fiber optic sensors included: Ion Laser Technology (Salt Lake City, Utah) argon ion laser; 514.5 nm laser band-pass filter (Newport Corp. Irvine, Calif.); Uniblitz shutter controller (Rochester, N.Y.); fiber coupler (Newport Corp. Irvine, Calif.); Olympus inverted fluorescence microscope, IMT-II (Lake Success, N.Y.); Nikon 50 mm f/1.8 camera lenses; Acton 150 mm spectrograph (Acton, Mass.); and, a Princeton Instruments 1024×256 LN2 cooled CCD array (Trenton, N.J.).

The results showed that, based on representative spectra of both the R-phycoerythrin and the Texas red labeled-bovine serum albumin, the proteins were immobilized onto the end of an optical fiber (data not shown). More importantly, although there is only a monolayer of fluorescent material on the surface of the optical fiber, a strong signal was measured (data not shown). Interestingly, the results indicate that the size of the gold colloid used in the sensor development plays a significant role in the amount of fluorescence signal obtained, with 100 nm particles showing what appear to be the best results (data not shown).

EXAMPLE 2

In this example, pulled sensors are described. Sub-micron sized fiber optic sensor were prepared by pulling multimedia fiber in a home-built puller consisting of a modified pipette-puller heated with a $CO_2$ laser. The pulled tips were then silanized, coated with aluminum in a home-built evaporator and prepared with gold colloid and protein as above.

EXAMPLE 3

Figure 2:
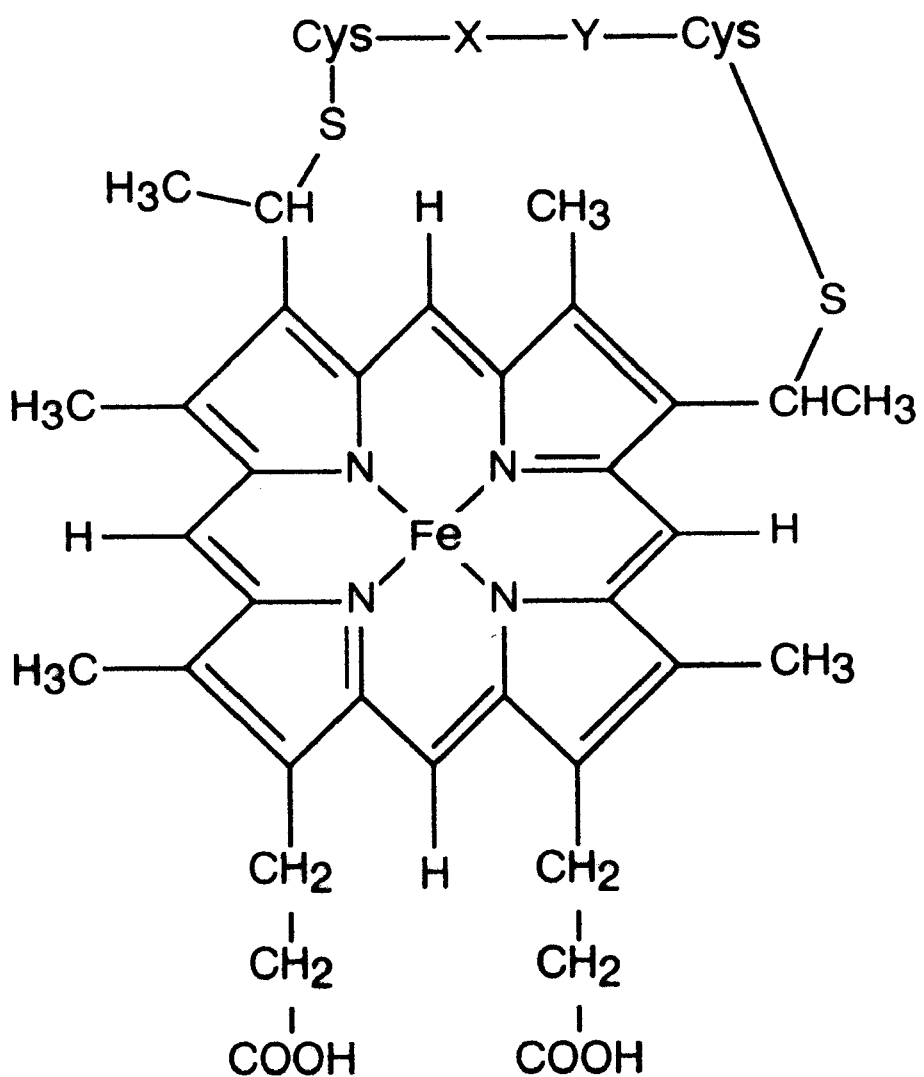
FIG. 2 shows the heme group of one embodiment of a nitric oxide-binding protein, i.e., cytochrome c'.

This example describes the first sensor to incorporate cytochrome c'. The heme group of this nitric oxide-binding protein is shown in FIG. 2. Cytchrome c' was chosen as the chemical recognition element because it exhibits spectral changes upon binding nitric oxide and is highly selective. While a precise understanding of the mechanisms involved is not necessary for the practice of the invention, it is believed that, as the sixth ligand site of cytochrome c' is buried within the protein, it is usually accessible only to carbon monoxide and nitric oxide. However, cytochrome c' undergoes autoxidation to Fe(III), which binds nitric oxide, but not carbon monoxide.

To prepare the sensor, 100 µm core diameter multimedia fibers (General Fiber Optics, Cedar Grove, N.J.) or multi-media fibers were pulled to a submicrometer tip diameter and were silanized for 2 hrs in neat 3-mercaptopropyl-trimethoxy silane (Gelest, Inc., Tullytown, Pa.) in a well-ventilated fume hood. The fibers were rinsed with methanol and water and placed in 50 nm gold colloid (Vector Labs, Inc., Burlingame, Calif.) for 3 hrs at 0° C. to form a self-assembled monolayer of gold colloids. The gold-coated fibers were immersed overnight in either a *Chromatium vinosum*, *Rhodocyclus purpureus*, or *Rhodocyclus gelatinosus* cytochrome c' solution prepared with pH 7.4 phosphate buffer at 15° C. to allow the cytochrome c' to adsorb to the surface of the gold via the protein amine groups. The fiber was then rinsed in buffer to remove any residual protein. Dye-labeled sensors were prepared with 4-carboxy-3,5,6 trifluoro-2',7',- difluorofluorescein, succinimidyl ester (Oregon Green™ 514 carboxylic acid, succinimidyl ester) purchased from Molecular Probes (Eugene, Oreg.). A 16 mM dye solution in DMSO was diluted to 1 M with 0.1 M $NaHCO_3$. The cytochrome c' sensors were soaked for 1 hr in the dye solution.

Figure 3B:
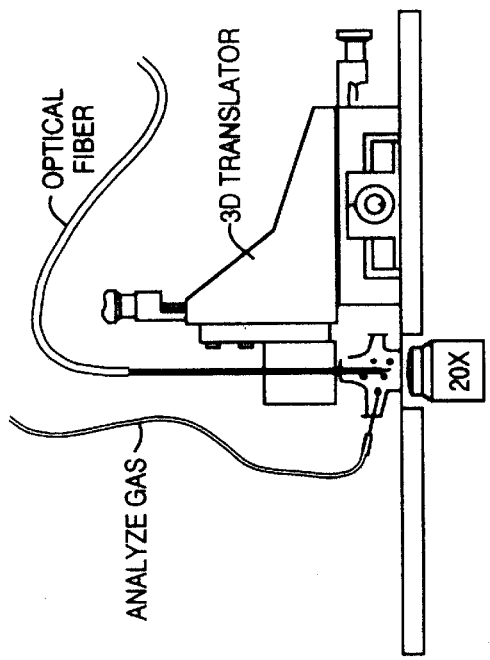
FIG. 3 shows one embodiment of an optical array useful for testing the sensors of the present invention.
Figure 3A:
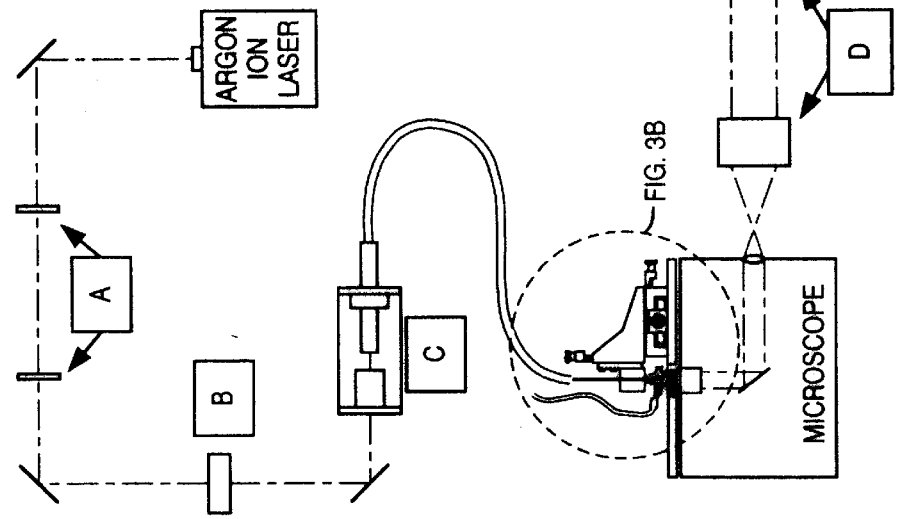

The gold colloid-containing sensors that were prepared with either *C. vinosum*, *R. purpureus*, or *R. gelatinosa* cytochromes c' were tested. One embodiment of the optical array useful for testing is shown schematically in FIG. 3).

Figure 4:
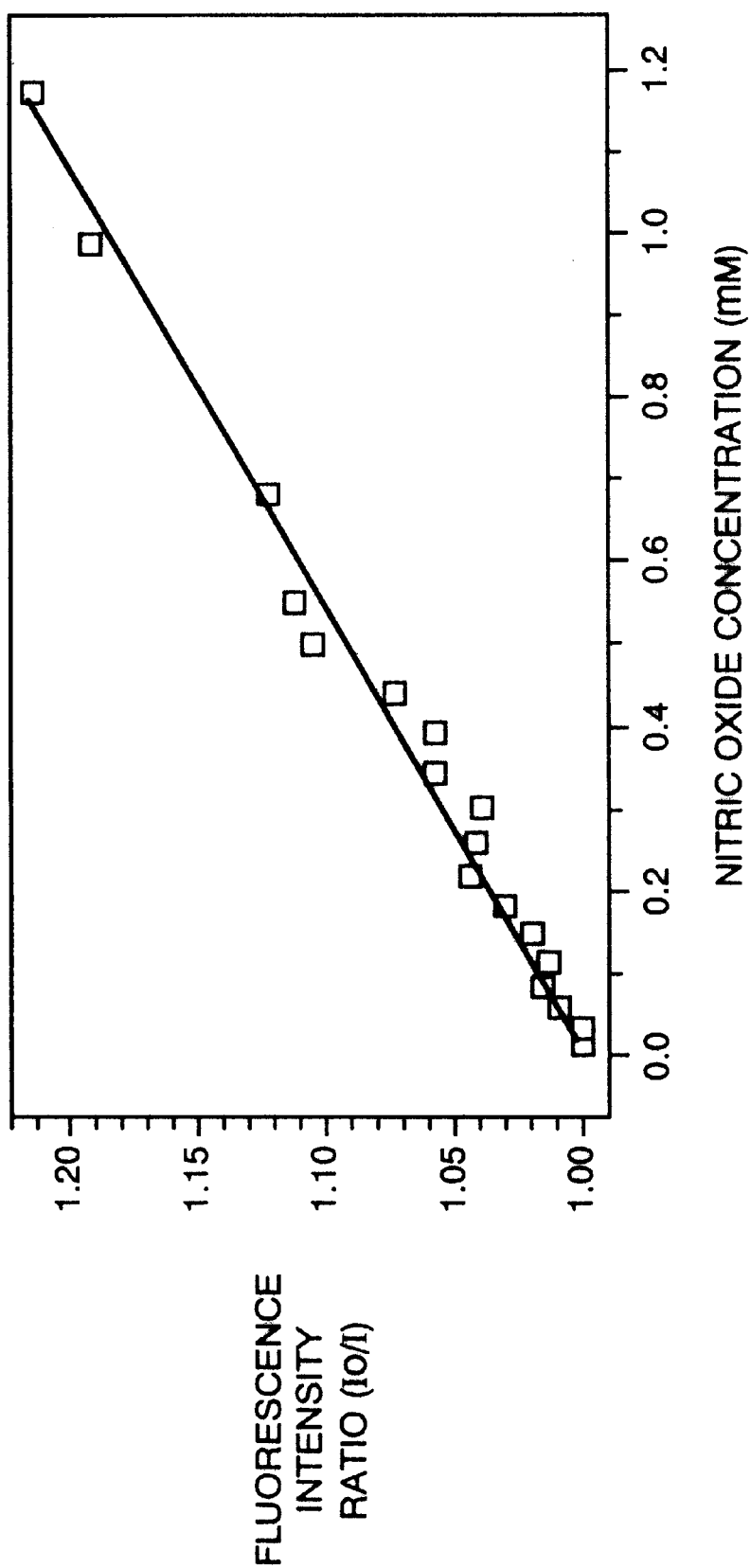
FIG. 4 is a graph showing the response of one embodiment of an optical fiber sensor of the present invention, said fiber having cytochrome c' of C. vinosum immobilized on gold colloid.
Figure 5:
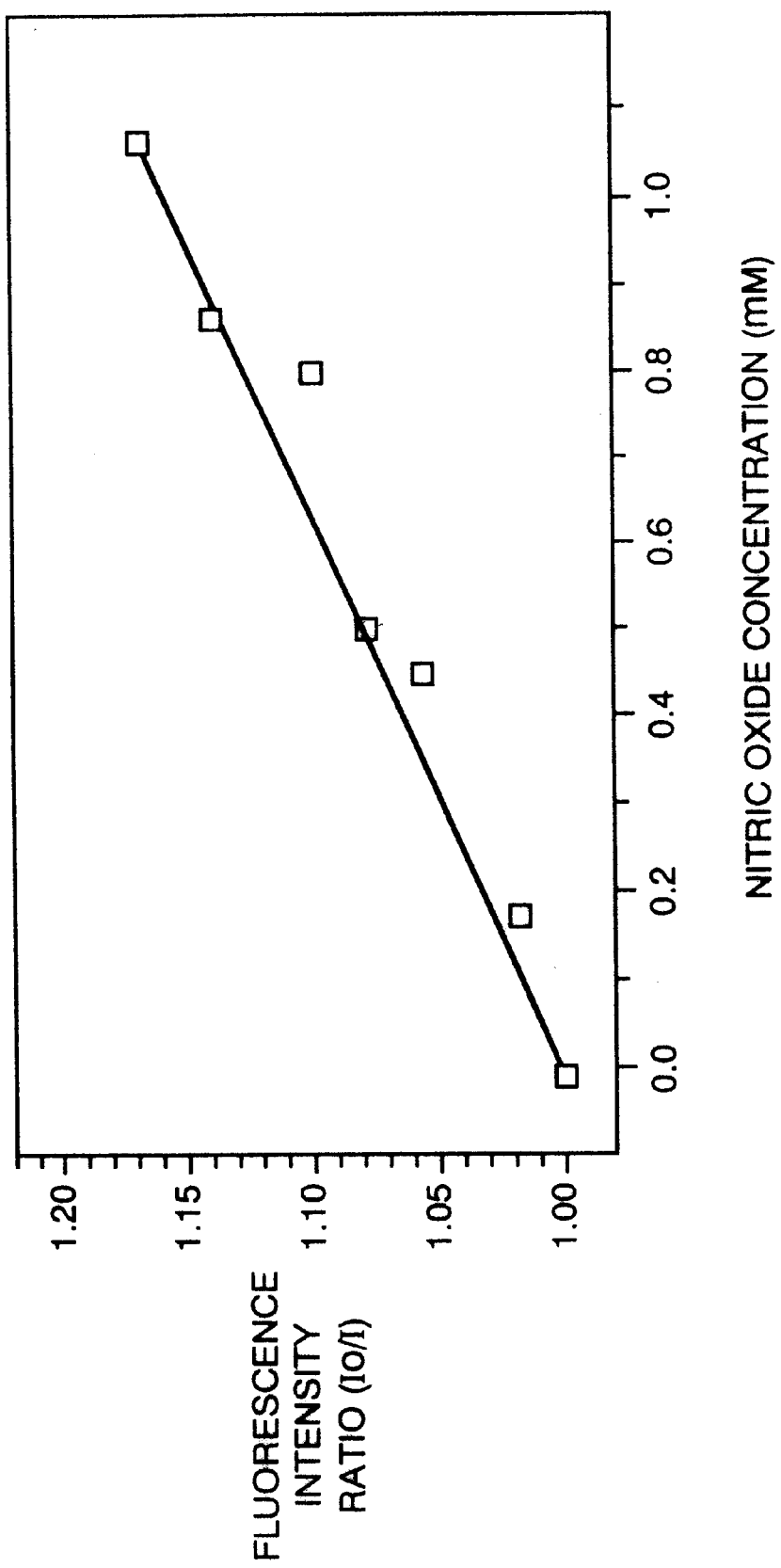
FIG. 5 is a graph showing the response of one embodiment of an optical fiber sensor of the present invention, said fiber having cytochrome c' of R. purpureus immobilized on gold colloid.
Figure 6:
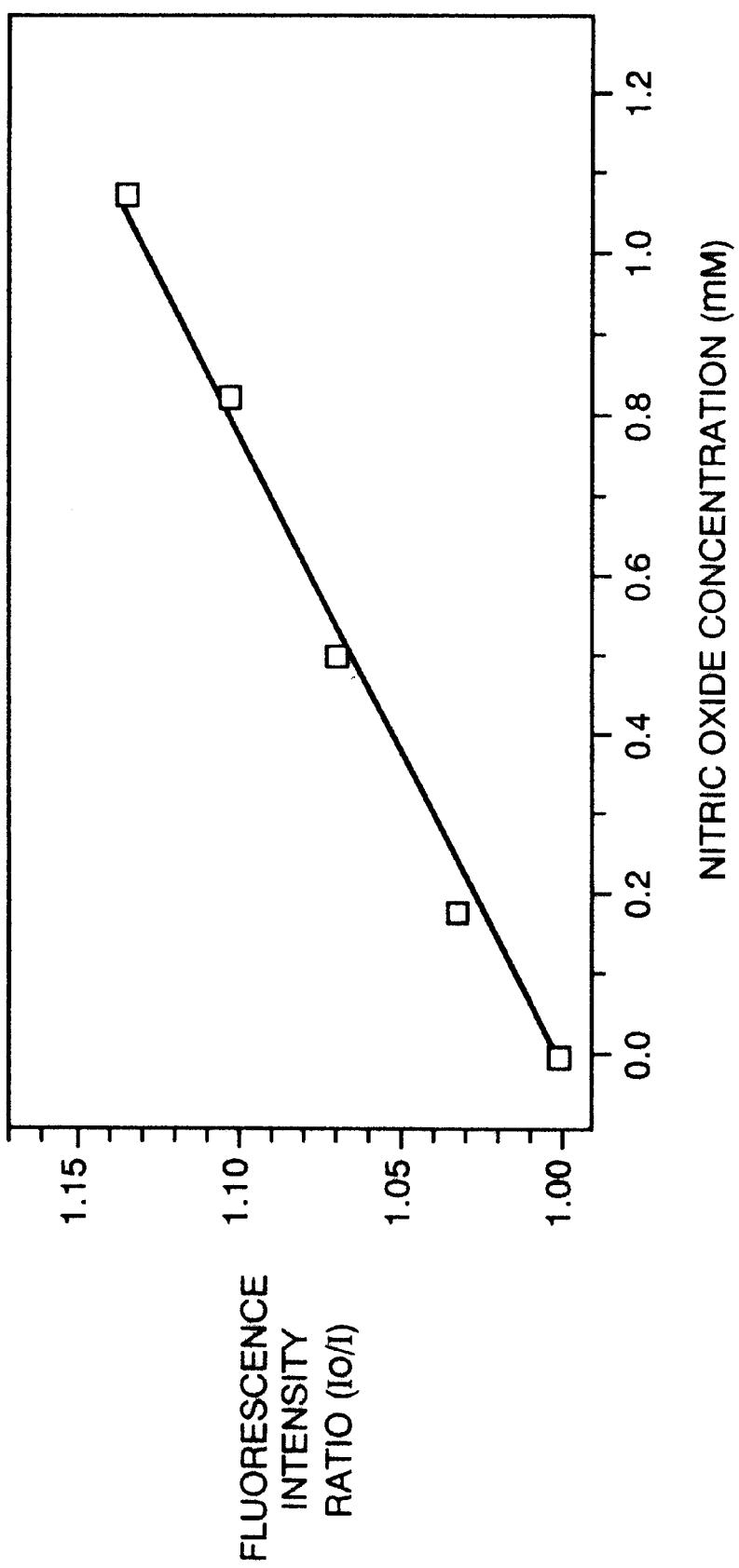
FIG. 6 is a graph showing the response of one embodiment of an optical fiber sensor of the present invention, said fiber having cytochrome c' of R. gelatinosa immobilized on gold colloid.
Figure 7:
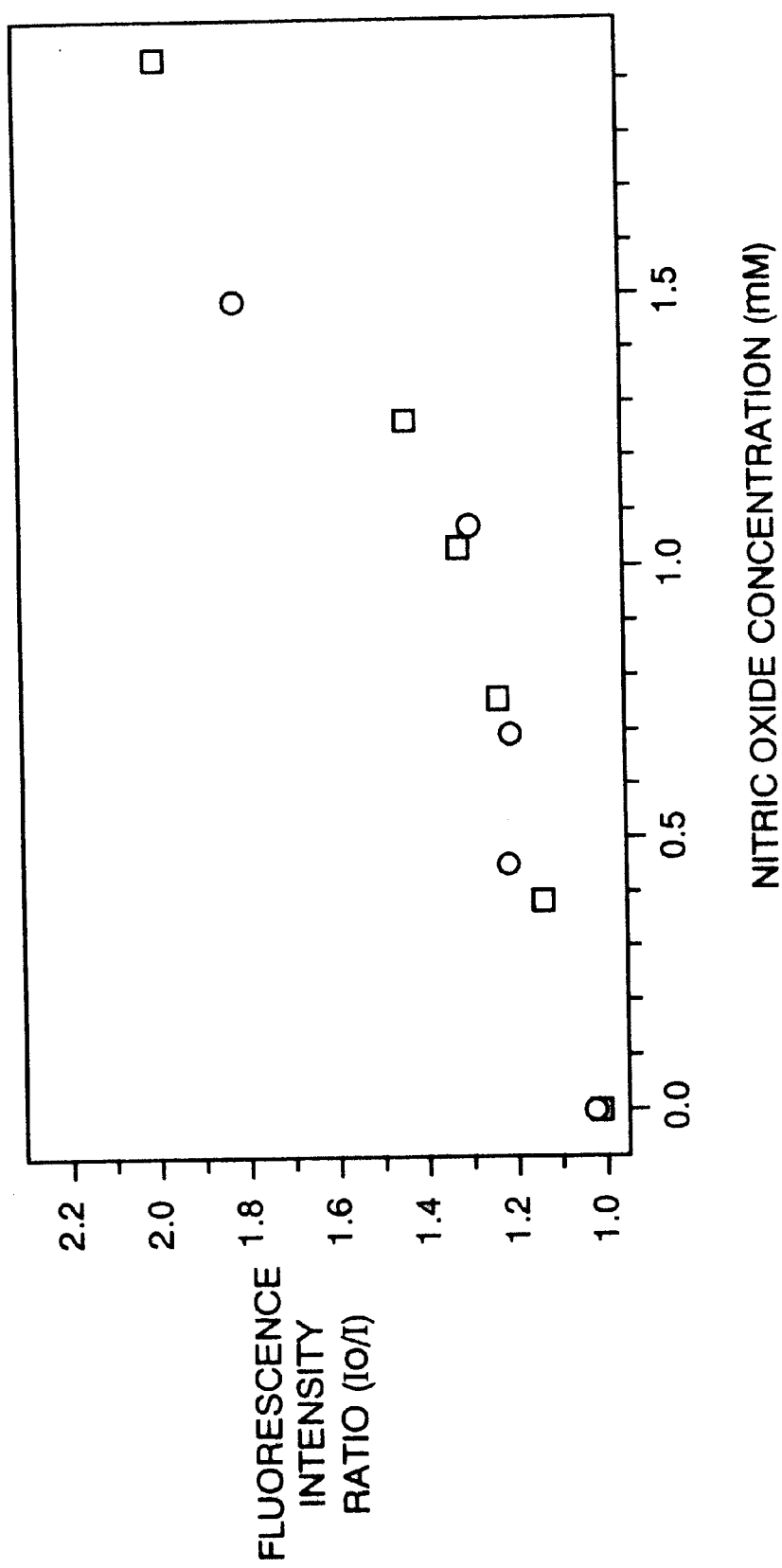
FIG. 7 shows the reversibility of one embodiment of the sensor of the present invention.

All three cytochromes c'-containing sensors were found to have linear responses up to 1 mM nitric oxide (FIGS. 4–6). Above this concentration is a second linear region with a slope which is three times that below 1 mM, as shown in FIG. 7. The steeper slope found at higher concentrations may be due to spectroscopic changes upon binding a second nitric oxide molecule per monomer, or may be caused by each cytochrome c' dimer binding more than two nitric oxide molecules. In view of their structural similarities, it is not surprising that all three cytochromes c' have comparable slopes. The *C. vinosum* (FIG. 7, where squares indicate increasing nitric oxide concentration and circles indicate decreasing nitric oxide concentration) and *R. purpureus* cytochromes c' are readily reversible. The *R. gelatinosa* cytochrome c' does not respond reversibly, but the reasons for this difference have not yet been determined. The present limit of detection is approximately 20 µM nitric oxide. While the reaction of *C. vinosum* cytochrome c' has been reported to be slow when measured in solution via absorbance, the results using the sensors of the present invention show that the sensor's response time is less than 2 seconds.

The *C. vinosum*, *R. purpureus*, and *R. gelatinosa* cytochromes c' sensors were tested for selectivity against common interfering chemicals. 1 M nitrate and nitrite, oxygen, nitrogen, and $1.5 \times 10^{-4}$ M ascorbic acid, in phosphate buffer solution, were found to have no effect on the sensor response (data not shown). Low µM riboflavin was found to interfere with dye-labeled sensors due to its fluorescence band in the 530 nm region, overlapping with that of the labeling dye. The addition of 4 µM riboflavin was equivalent to a 30 µM decrease in nitric oxide concentration. However, riboflavin does not affect the cytochrome c' fluorescence. Dopamine at high levels also interfered with the detection of nitric oxide. In solution, dopamine was found to cause a blue shift in the protein fluorescence. For sensors prepared without the labeling dye, the addition of 140 mM dopamine was, on average for the three cytochromes c', equivalent to the addition of 0.1 mM nitric oxide. For the dye-labeled sensors, 0.25 mM dopamine was, on average, equivalent to the addition of 0.1 mM nitric oxide. Sensors made with the cytochromes c' alone (without dye labeling) were not affected by pH between pH 3–10. The dye fluorescence is sensitive to pH below 7. In solution, hydrogen peroxide caused an attenuation of the cytochrome c' fluorescence, but no spectral shift. Dye-labeled sensors exhibited an average signal increase of 4% in 1M hydrogen peroxide, equivalent to the removal of 0.2 mM nitric oxide. However, the concentration of oxygen radicals needed to interfere with the sensor response is higher than that found in many biological systems.

EXAMPLE 4

In this example, a heme-binding protein is prepared and attached to a metal monolayer of a fiber tip. The heme-binding protein prepared is the protein that been isolated and characterized from both the hemolymph and oocytes of the blood-sucking insect, *Rhodnius prolixus*. See generally P. L. Oliveira et al., "A Heme-binding Protein from Hemolymph and Oocytes of the Blood-sucking Insect, *Rhodnius prolixus*," *J. Biol. Chem.* 270:10897 (1995). The Rhodnius heme-binding protein (RHBP) is composed of a single 15-kDa polypeptide chain coiled in a highly a-helical structure which binds non-covalently one heme/polypeptide chain. This RHBP is not produced by limited degradation of hemoglobin from the vertebrate host, since specific polyclonal antibodies against it do not cross-react with rabbit hemoglobin, and since it differs from hemoglobin in having a distinct amino-acid composition and $NH_2$-terminal sequence. The spectrum of the dithionite-reduced protein has peaks at 426, 530, and 559 nm and resembles that of a b-type cytochrome.

RHBP from hemolymph is not saturated with heme and promptly binds heme added to the solution. The oocyte protein, on the other hand, is fully saturated and is not capable of binding additional heme.

For preparation of the protein, insects are taken from a colony of *R. prolixus* maintained at 28° C. and 70% relative humidity. Normal mated females are fed on rabbit blood at 2-week intervals. Four to 6 days after a meal, hemolymph is collected in the presence of phenylthiourea (30–130 μg/ml), 5 mM EDTA, and a mixture of protease inhibitors prepared in 0.15 M NaCl, with final concentrations of 0.05 mg/ml of soybean trypsin inhibitor, leupeptin, lima bean trypsin inhibitor and antipain, and 1 mM benzamidine. On the same day, chlorinated oocytes are dissected and washed with ice-cold 0.15 M NaCl in order to remove ovarian debris prior to homogenization. Oocytes are homogenized in a Potter-Elvehjem homogenizer in the presence of the same mixture of protease inhibitors, buffered with 20 mM Tris-HCl, pH 7.0, (approximately 500 oocytes to 1 ml), and centrifuged at room temperature in a microcentrifuge at 11,000×g for 5 min. The floating lipids and the pellet are discarded, and the clear supernatant is used as the crude oocyte extract for protein purification.

Solid ammonium sulfate is added to bring the oocyte extract to 45% saturation, and the suspension is gently stirred for 20 min at 4° C. After centrifugation at 11,000×g for 10 min, the precipitate is discarded, and the supernatant is brought to 60% saturation. This new precipitate is then washed twice with a 60% saturated ammonium sulfate solution and then back-extracted by resuspending in a 45% saturated solution and centrifuging. The pellet is discarded and the supernatant is dialyzed against 0.15 M NaCl, 10 mM Tris-HCl, pH 7.0, and applied to a column of Sephadex G-200 (2.5×55 cm) equilibrated with the same solution. Protein content of fractions is measured by the absorbance- at 280 nm. The colored fractions containing RHBP are pooled, dialyzed against deionized water, and lyophilized.

Hemolymph (approximately 3 ml) is diluted to 5 ml with phosphate-buffered saline (0.15 M NaCl, 0.1 M sodium phosphate, pH 7.0) and 1.25 g of KBr is added. The solution is centrifuged at 80,000×g for 20 h at 4° C. The fractions at the bottom of the tube are collected and dialyzed against deionized water until an abundant precipitate forms. The solutions is then centrifuged at 11,000×g for 10 min at 4° C. The supernatant is brought to 10 mM with Tris base and applied to a column (1.5×18 cm) of DEAE-Toyopearl, equilibrated with 10 mM Tris-HCl, pH 8.4. The column is first washed with 20 ml of the same buffer and then eluted with and NaCl gradient (0–100 mM). The fractions containing RHBP are pooled and applied to a Sephadex G-75 column (1.5×80 cm) equilibrated with 0.15 M NaCl, 10 mM Tris-HCl, 7.0. Fractions containing the RHBP are pooled, dialyzed against deionized water, and lyophilized.

Proteins from both sources are monomeric, as indicated by an apparent molecular weight of between approximately 12,000 and 15,000. The purified protein (0.01%) is added to metal colloid as described above for the other proteins.

EXAMPLE 5

In this example, a nitric-oxide-carrying hemoprotein is prepared from a salivary gland homogenate of the bedbug *Cimex Lectularius*. The insect colonies are maintained at 27 C and 65% humidity. Insects are fed every 10 days by exposing them to the shaved abdomen of an anesthetized rabbit. Salivary glands of insects at 8–10 days after feeding are dissected and stored in buffers or used immediately. In any event, they are disrupted with a dissection needle and the homogenate centrifuged in the cold at 14,000 RPM for 5 minutes. The supernatants are recovered and used for binding to metal colloids as described above.

The salivary gland homogenates have a nitrosyl-hemoprotein that releases nitric oxide in a pH-dependent manner. The fraction containing the NO-carrying hemoprotein, when separated by HPLC, causes vasodilation of a preconstricted rabbit aortic strip.

EXAMPLE 6

This example describes the preparation of soluble guanylate cyclase ("sGC"). See generally Stone and Marletta, "Soluble Guanylate Cyclase from Bovine Lung: Activation with Nitric Oxide and Carbon Monoxide and Spectral Characterization of the Ferrous and Ferric States," *Biochemistry* 33:5636 (1994). sGC can be purified from bovine lung. Steps should be performed at 4° C. During the purification, assays for sGC can be carried out in 50 mM TEA, pH 7.4, with 2 mM DTT, m $MnCl_2$, 100 μM GTP, 1 mM IBMX, m phosphocreatine, and 152 units/L creatine kinase, with or without 100 μM sodium nitroprusside (SNP) in a total volume of 100 μL at 37° C. The assays are quenched with 400 μL of 125 mM $Zn(CH_3COO)_2$ and 500 μL of 125 mM $Na_2CO_3$. The amount of cGMP generated can then be quantified via radioimmunoassay (Amersham). After each column, only active fractions which can be activated at least 10-fold with SNP are carried on to the subsequent step.

Fresh bovine lung (1100 g) is homogenized with a food processor in 1100 mL of homogenizing buffer (25 mM TEA, m DTT, lmM PMSF, 1 mM EDTA, 0.2 mM benzamidine, 1 μM pepstatin A, 1 μM leupeptin, pH 7.8). The homogenate is then centrifuged at 100000×g for 60 min. The resulting supernatant is added to 450 mL of DEAE-Sepharose CL-6B and stirred slowly with an overhead stirrer for 45 min. The buffer is removed by vacuum filtration, and the resin washed four times by stirring slowly for 15 min with 1200 mL of homogenizing buffer. The resin is then poured into a 2.5× 100 cm column and packed by washing the column with homogenizing buffer for 1 h at 80 mL/h. sGC is then eluted with 1 L of a 0.0–0.4 M NaCl gradient at 80 mL/h. Active fractions are pooled (140 mL) and dialyzed for 8 h against 4 L of 25 mM TEA, 5 mM DTT, 0.1 mM PMSF; 0.2 Mm benzamidine, 1 μM pepstatin A, 1 μM leupeptin, ph 7.4.

The sample is then brought to m $MnCl_2$ and applied μ 25 mL/h to a 75-mL column of ATP-agarose (11-atom spacer attached through C-8). The column is washed at 25 mL/h with 150 mL of buffer A (25 mM TEA, mM DTT; 1 mM PMSF, 0.2 mM benzamidine, 5 mM $MnCl_2$, pH 7.4). The column is then washed at 50 mL/h with 200 mL of buffer A containing 10 mM $NaNO_3$, 10 mM creatine, and m ADP followed by 300 mL of buffer A. sGC is then eluted at 50 mL/h with a 2-L gradient running from 5 mM $MnCl_2$ to 1 mM EDTA. Active fractions are pooled (200 mL), concentrated by ultrafiltration to 30 mL on a YM-30 membrane (Amicon), and brought to 5 mM $MnCl_2$.

The sample is then applied at 5 mL/h to a 3.0-mL column of GTP-agarose (11-atom spacer attached through ribose hydroxyls, ICN). The column is washed at 5 mL/h with 10-mL of buffer A, and then sGC is eluted with a 100-mL gradient running from 0.0 to 0.4 M NaCl in buffer A. Active fractions are pooled, concentrated by ultrafiltration to 8 mL on an Omega Series membrane (30 kDA MWCO, Filtron), and applied to a 2.5×95 cm column of Ultrogel AcA-34 (IBF) at 20 mL/h. The column is then washed with 400 mL of 25 mM TEA, m DTT pH 7.8 at 20 mL/h. Active fractions are pooled (20 mL), provided with additional DTT (5 mM final), brought to 1.0 M NaCl, and concentrated by ultrafiltration to 1.0 mL on an Omega Series membrane. The sample is brought to 50% glycerol and stored as aliquots under nitrogen at −70° C.

The above-described purification scheme results in the isolation of approximately 0.5 mg of sGC from 1100 g of bovine lung. Following the procedure, two bands should be visible on reducing SDS-PAGE of approximately equal intensity with apparent masses of 69 and 78 kDA. The protein prepared as described above can then be immobilized on metal colloids.

EXAMPLE 7

This example describes the preparation of macro-sensors (sensors made on larger substrates, i.e., larger than fiber optic sensor tips). The sensor was made on glass microscope slides cleaned by immersion in piranha solution (10:1 sulfuric acid:hydrogen peroxide), copious rinsing in triply distilled water and oven drying. The glass was then silanized in a 10% solution of 3-(mercatopropyl) trimethoxysilane in methanol for 24 hours. The glass was rinsed with methanol, then tripley distilled water. The silanized glass was placed in colloidal gold (used as received from the manufacturer) for 24 hours, then rinsed with water. For comparison of sizes of gold colloids, six different gold sizes were used: 5, 10, 20, 50, 100 and 250 nm.

EXAMPLE 8

This example describes the preparation of a sensor comprising a fluorescein derivative dye attached to colloidal gold. Specifically, sensors were prepared using 100 μm core diameter multimedia fibers (Polymicro Technologies) which were silanized for 2 hrs. in neat 3-mercaptopropyltrimethoxy silane (Gelest, Inc.) in a well-ventilated fume hood. The fibers were rinsed with methanol and water and placed in 50 nm gold colloid (BBI, International) for 3 hrs at 0° C. to form a self-assembled monolayer of gold colloids, as confirmed by scanning electron microscopy (SEM). The gold-coated sensors were immersed 1 hr. in 20 mM 4-carboxy-2',7',-difluorofluorescein, succinimidyl ester (Oregon Greene™ 488 carboxylic acid, succinimidyl ester, Molecular Probes) in DMSO. The sensors were then rinsed in distilled water.

EXAMPLE 9

This example describes the alternative preparation of a sensor comprising a fluorescein derivative dye attached to colloidal gold. Specifically, sensors were prepared using 0.5×4.5 cm² quartz slides which were silanized for 2 hrs. in neat 3-mercaptopropyltrimethoxy silane (Gelest, Inc.) in a well-ventilated fume hood. The slides were rinsed with methanol and water and placed in 50 nm gold colloid (BBI, International) for 3 hrs at 0° C. to form a self-assembled monolayer of gold colloids, as confirmed by scanning electron microscopy (SEM). The gold-coated sensors were immersed 1 hr. in 20 mM 4-carboxy-2',7',-difluorofluorescein, succinimidyl ester (Oregon Green™ 488 carboxylic acid, succinimidyl ester, Molecular Probes) in DMSO. The sensors were then rinsed in distilled water.

EXAMPLE 10

This example describes an alternative preparation of a sensor comprising a fluorescein derivative dye attached to colloidal gold. Specifically, sensors were prepared using 100 μm core diameter multimedia fibers (Polymicro Technologies) which were silanized for 2 hrs. in neat 3-mercaptopropyltrimethoxy silane (Gelest, Inc.) in a well-ventilated fuime hood. The fibers were rinsed with methanol and water and placed in 50 nm gold colloid (BBI, International) for 3 hrs at 0° C. to form a self-assembled monolayer of gold colloids, as confirmed by scanning electron microscopy (SEM). The gold-coated sensors were immersed 1 hr. in 20 mM 4-carboxy-2',7',-difluorofluorescein, succinimidyl ester (Oregon Green™ 488 carboxylic acid, succinimidyl ester, Molecular Probes) in DMSO. The sensors were then rinsed in distilled water. To the fiber sensors 40 nm fluorescent carboxylate-modified polystyrene microspheres with 488 nm excitation and 685 nm emission (TransFluoSpheres™ Molecular Probes) were then added by dipping the sensor in a dilute suspension of the spheres (0.002% solids). The sensors were rinsed in distilled water.

EXAMPLE 11

This example describes an alternative preparation of a sensor comprising a fluorescein derivative dye attached to colloidal gold. Specifically, sensors were prepared using 0.5×4.5 cm² quartz slides which were silanized for 2 hrs. in neat 3-mercaptopropyltrimethoxy silane (Gelest, Inc.) in a well-ventilated fume hood. The slides were rinsed with methanol and water and placed in 50 nm gold colloid (BBI, International) for 3 hrs at 0° C. to form a self-assembled monolayer of gold colloids, as confirmed by scanning electron microscopy (SEM). The gold-coated sensors were immersed 1 hr. in 20 mM 4-carboxy-2',7',-difluorofluorescein, succinimidyl ester (Oregon Greene™ 488 carboxylic acid, succinimidyl ester, Molecular Probes) in DMSO. The sensors were then rinsed in distilled water. To the fiber sensors 40 nm fluorescent carboxylate-modified polystyrene microspheres with 488 nm excitation and 685 nm emission (TransFluoSpheres® Molecular Probes) were then added by dipping the sensor in a dilute suspension of the spheres (0.002% solids). The sensors were rinsed in distilled water.

EXAMPLE 12

In another example, sensors were prepared according to the following method. *Chromatium vinosum* cytochrome c' was labeled with 4-carboxy-2',7',-difluorofluorescein, succinimidyl ester (Oregon Green™ 488 carboxylic acid, succinimidyl ester) purchased from Molecular Probes according to product information procedures. 1 mg of cytochrome c' was dissolved in 0.1 M NaHCO$_3$. The 20 mM dye solution was prepared in DMSO. 5 mL dye solution was added to the cytochrome c' solution and the mixture was allowed to react for 1 hr. at room temperature. The free dye was separated from the dye-labeled protein on a Sephadex G-25 (Sigma) column with 100 mM pH 7.4 phosphate buffer as the mobile phase. Fiber sensors were prepared according to the method of Clark, et al. using 100 μm core diameter multimedia fibers (Polymicro Technologies) which were silanized for 2 hrs. in neat 3-mercaptopropyltrimethoxy silane (Gelest, Inc.) in a well-ventilated fume hood. The fibers were rinsed with methanol and water and placed in 50 nm gold colloid (BBI, International) for 3 hrs at 0° C. to form a self-assembled monolayer of gold colloids, as confirmed by scanning electron microscopy (SEM). The gold-coated fibers were immersed 1–2 hrs. in the dye-labeled cytochrome c' solution to allow the cytochrome c' to adsorb to the surface of the gold via the protein amine groups. Fluorescent carboxylate-modified polystyrene microspheres (40 nm) with 488 nm excitation and 685 nm emission (TransFluoSpheres, Molecular Probes) were then added by dipping the sensor in a dilute suspension of the spheres (0.002% solids). The sensors were rinsed in 100 mM pH 7.4 phosphate buffer.

From the above, it should be clear that the methods, devices and compositions of the present invention permit for the design of sensors that have excellent selectivity, reversibility, fast response time, and can be reduced to submicrometer scale for use in single-cell or other in vitro applications.

TABLE 1

| potential interference | sensor response |
|---|---|
| 1 M $NO_2^-$ | none |
| 1 M $NO_3^-$ | none |
| 100% $O_2$ | none |
| pH > 6$^b$ | none |
| 18 μM $H_2O_2$ | 2% signal increase |
| 3 μM $O_2^-$ | 4% signal increase |
| 6 μM $OONO^-$ | 1% signal decrease |

TABLE 2

| cell treatment | NO concn (μM) |
|---|---|
| none | <20 |
| IFN-γ and LPS | 190 ± 70 |
| IFN-γ, LPS, and NMMA | ≤20 |

What is claimed is:

1. An optical fiber comprising a fiber tip, said tip comprising an immobilized nitric oxide-binding compound and a fluorescent reference compound.

2. The optical fiber of claim 1, wherein said fiber tip is treated so as to have reactive groups and said nitric oxide-binding compound is covalently linked directly to said fiber via said reactive groups.

3. The optical fiber of claim 1, wherein said fiber tip is coated with an inert coating and said nitric oxide-binding compound is immobilized on said coating.

4. The optical fiber of claim 3, wherein said inert coating comprises a metal layer.

5. The optical fiber of claim 4, wherein said metal layer is a monolayer.

6. The optical fiber of claim 5, wherein said metal monolayer is non-linear.

7. The optical fiber of claim 6, wherein said metal monolayer comprises spherical metal particles.

8. The optical fiber of claim 7, wherein said metal particles comprise metal selected from the group consisting of gold, silver, tungsten, thoriasol, antimony pentoxide, carbon, red iron oxide, titanium dioxide and platinum.

9. The optical fiber of claim 1 wherein said nitric oxide-binding compound is a protein selected from the group consisting of porphyrin group- and heme group-containing proteins, and fragments thereof.

10. The optical fiber of claim 9, wherein said nitric oxide-binding compound is the heme group-containing protein cytochrome c'.

11. The optical fiber of claim 10, wherein said cytochrome c' is purified cytochrome c' from a bacteria.

12. The optical fiber of claim 11, wherein said bacteria is selected from the group consisting of purple phototropic bacteria, aerobic nitrogen-fixing bacteria, and facultatively denitrifying bacteria.

13. The optical fiber of claim 12, wherein said bacteria is selected from the group consisting of C. vinosum, R. purpureus, and R. gelatinosa.

14. The optical fiber of claim 9, wherein said nitric oxide-binding compound is the heme group-containing protein guanylate cyclase.

15. The optical fiber of claim 9, wherein said guanylate cyclase is bovine lung quanylate cyclase.

16. The optical fiber of claim 1, wherein said nitric oxide-binding compound is a heme-binding protein.

17. The optical fiber of claim 16, wherein said heme-binding protein is dye-labeled.

18. The optical fiber of claim 16, wherein said heme-binding protein is an insect heme-binding protein.

19. The optical fiber of claim 18, wherein said heme-binding protein is the heme-binding protein of Rhodnius prolixus.

20. The optical fiber of claim 1, wherein said nitric oxide-binding compound is a protein selected from the group consisting of dye-labeled, porphyrin group- and dye-labeled, heme group-containing proteins, and fragments thereof.

21. The optical fiber of claim 1, wherein said fluorescent reference compound comprises a microsphere.

22. The optical fiber of claim 21, wherein said microsphere is a carboxylate-modified polystyrene.

23. The optical fiber of claim 22, wherein said polycarboxylate-modified polystyrene presents a 488 nm excitation and 685 nm emission spectral profile.

* * * * *